(12) United States Patent
Lee et al.

(10) Patent No.: US 7,645,466 B2
(45) Date of Patent: Jan. 12, 2010

(54) METHODS FOR DERIVING, ISOLATING, AND/OR EXTRACTING AMINO ACID COMPOSITIONS FROM FENUGREEK SEED

(75) Inventors: Steve S. Lee, Sandy, UT (US); Richard B. Hynson, Missoula, MT (US); Ke-Qin Zhang, Fujian (CN); Wu-Zhou Li, Jiangsu (CN); Jing S. Zhou, Shanghai (CN)

(73) Assignee: TSI Group Limited, Central Hong Kong (CN)

( * ) Notice: Subject to any disclaimer, the term of this patent is extended or adjusted under 35 U.S.C. 154(b) by 181 days.

(21) Appl. No.: 11/069,747

(22) Filed: Mar. 1, 2005

(65) Prior Publication Data
US 2005/0238738 A1   Oct. 27, 2005

Related U.S. Application Data

(60) Provisional application No. 60/549,182, filed on Mar. 2, 2004, provisional application No. 60/549,305, filed on Mar. 2, 2004.

(51) Int. Cl.
*A61K 36/48* (2006.01)
(52) U.S. Cl. .................................................. 424/757
(58) Field of Classification Search ........................ None
See application file for complete search history.

(56) References Cited

U.S. PATENT DOCUMENTS

| | | | |
|---|---|---|---|
| 5,449,823 A | | 9/1995 | Lerch |
| 5,470,879 A | * | 11/1995 | Sauvaire et al. ............. 514/561 |
| 5,658,571 A | | 8/1997 | Gopalan et al. |
| 5,997,877 A | | 12/1999 | Chang |
| 6,413,546 B1 | | 7/2002 | He et al. |
| 2001/0024665 A1 | * | 9/2001 | Rao et al. .................... 424/757 |

FOREIGN PATENT DOCUMENTS

| | | |
|---|---|---|
| EP | 0587476 | 3/1994 |
| WO | WO 97/32577 | 9/1997 |
| WO | WO 99/25197 | 5/1999 |
| WO | WO 01/15689 | 3/2001 |

OTHER PUBLICATIONS

Room Temperature . retrieved from the internet <http://en.wikipedia.org/wiki/Room_temperature>. retrieved on Apr. 4, 2008.*
URL: http://www.tsiinc.com/products/brand/phtml?brand_id=19 (Accessed May 21, 2003) Promilin product information.
URL: http://www.airgreen.co.jp/fenugreek/index_e.html (Accessed Jan. 16, 2003) Fenugreek.
Belongie L, "Syndrome X Analyzed," HSR Health Supplement Retailer, Apr. 2002.
URL: http://www.sabinsa.com/products/fenusterl.htm (Accessed Apr. 4, 2002).
URL:http://www.kbcincusa.com/BrandNameProducts/Sterofen/STEROFENSpec.htm (Accessed Apr. 2, 2002) Sterofen.
URL: http://www.finsupplements.com/search/Details.asp?RefSite=altdia&ProductID=6 (Accessed Mar. 26, 2002) Natures Way Blood Sugar with Gymnema.
URL: http://www.chromadex.com/Phytosearch/Fenugreek.htm (Accessed Jan. 17, 2002) Fenugreek.
Billaud et al. "Fenugreek: composition, nutritional value and physiological properties," Sciences des Aliments 2001; 21(1): 3-26.
Zupancic et al., "The impact of fertilization on fenugreek yield (*Troginella foenum-graecum* L.) and diosgenin content in the plant drug," Rostl Vyroba 2001; 47.
Liu F et al., "An extract of *Langerstroemia speciosa* L. has insulin-like glucose uptake-stimulatory and adipocyte differenctiation-inhibitory activities in 3T3-L1 cells," Journal of Nutrition 2001; 131(9): 2242-7.
Breil et al., "Effect of 4-hydroxyisoleucine on insulin sensitivity in insulin resistant rats," European Association for the Study of Diabetes, 37th Annual Meeting, Glasgow, United Kingdom, Sep. 9-13, 2001, Abstract: 300.
Andrich VS, "Sports Supplement Review. The Lowdown on Insulin Amplifiers and Glycemic Response Modifiers," Muscle Media Article, Jan.-Feb. 2001.
Garti et al., "Fenugreek Gum. The magic fiber for an improved glucose response and cholesterol reduction," Jan. 2001; 1(3): 5-10.
Van Loon LJC et al., "Maximizing postexercise muscle glycogen synthesis: carbohydrate supplementation and the application of amino acid or protein hydrolysate mixtures," URL: http://www.acjn.org/cgi/content/abstract/72/1/106 (Accessed Mar. 26, 2002), American Journal of Clinical Nutrition, Jul. 2000; 72(1): 106-11.
Van Loon LJC et al., "Plasma insulin responses after ingestion of different amino acid or protein mixtures with carbohydrate," URL: http://www.acjn.org/cgi/content/abstract/72/1/96 (Accessed Mar. 26, 2002), American Journal of Clinical Nutrition, Jul. 2000; 72(1): 96-105.
Kassem T. et al., "Two key chiral intermediates in a new 4-hydroxyisoleucine synthesis," Acta Crystallographica 2000; C56: 1037-9.

(Continued)

*Primary Examiner*—Patricia Leith
*Assistant Examiner*—Melenie McCormick
(74) *Attorney, Agent, or Firm*—Marshall, Gerstein & Borun LLP

(57) ABSTRACT

The present invention is directed to novel compositions of bio-active compounds comprising 4-hydroxyisoleucine and one or more compounds selected from the group of amino acids, alkaloids, glycosides, volatile oils, saponins, sapogenins, mannans, flavonoids, fatty acids, vitamins and provitamins, minerals, and carbohydrates. Preferably, the novel compositions of bio-active compounds include 4-hydroxyisoleucine and one or more amino acids selected from the group consisting of arginine, aspartate, threonine, serine, glutamate, proline, glycine, alanine, cysteine, valine, methionine, isoleucine, leucine, tryptophan, phenylalanine, omithine, proline, lysine, histidine, and gamma-aminobutyrate. The composition of bio-active compounds preferably include between about ten percent and about seventy percent of 4-hydroxyisoleucine and between about twenty percent and about forty percent of other amino acids. The bio-active compounds of the novel composition of the present invention may be derived, isolated, and/or extracted from Fenugreek seeds.

16 Claims, 5 Drawing Sheets

OTHER PUBLICATIONS

Huang et al., "Determination of two flavone glycosides in the seeds of *Trigonella foenum-graecum* L. from various production locality," Zhiwu Ziyuan Yu Huanjing Xuebao 2000; 9(4): 53-4.

Broca C. et al., "4-hydroxyisoleucine: Effects of synthetic and natural analogues on insulin secretion," European Journal of Pharmacology 2000; 390: 339-345.

Blmenthal M.(ed), "Fenugreek Seed," Herbal Medicine: Expanded Commission E Monographs, American Botanical Council 2000.

Plesman J., "Fenugreek Stabilizes Blood Sugar Levels in Hypoglycemics and Diabetics," Hypoglycemic Health Newsletter. 2000; 16(1): 9-12.

Broca C. et al., "4-hydroxyisoleucine: experimental evidence of its insulinotropic and antidiabetic properties," American Journal of Physiology Oct. 1999; 277(4 Pt 1): E617-23.

Muralidhara et al., "Acute and subchronic toxicity assessment of debitterized fenugreek powder in the mouse and rat," Food and Chemical Toxicology 1999; 37(8): 831-8.

Genet et al., "Effects of vandate, insulin and fenugreek (*Trigonella foenum greacum*) on creatine kinase levels in tissues of diabetic rat," Indian Journal of Experimental Biology Feb. 1999; 37(2): 200-2.

Raju et al.,"Effect of antidiabetic compounds on glyoxalase I activity in experimental diabetic rat liver," Indian Journal of Experimental Biology Feb. 1999; 37(2): 193-5.

Szentimihalyi et al., "Investigation of *Troginella foenum-graecum* L. Fabacea oil. Comparative evaluation of samples from supercritical and conventional extraction," Olaj, Szappan, Kozmet 1999; 48(5): 204-6.

Panda et al., "Inhibition of triiodothyronine production by fenugreek seed extract in mice and rats," Pharmacological Research Jan. 1999; 40(5): 405-9.

Ravikumar et al., "Effect of fenugreek seeds on blood lipid peroxidation and antioxidants in diabetic rats," Phytotherapy Research May 1999; 13(3): 197-201.

Sowmya et al. ,"Hypocholesterolemic effect of germinated fenugreek seeds in human subjects," Plant Foods for Human Nutrition 1999; 53(4): 359-65.

Sauvaire Y. et al., "4-hydroxyisoleucine: A novel amino acid potentiator of insulin secretion," Diabetes 1998; 47: 206-10.

Puri D., "Therapeutic potentials of fenugreek," Indian Journal of Physiology and Pharmacology Jul. 1998; 42(3): 423-4.

Taylor et al., "Analysis of steroidal sapogenins from Amber Fenugreek (*Trigonella foenum-graecum*) by capillary gas chromatography and combined gas chromatography/mass spectrometry," Journal of Agricultural and Food Chemistry 1997; 45(3): 753-9.

Bordia et al., "Effect of ginger (*Zingiber officinale* Rosc.) And fenugreek (*Trigonella foenumgraecum* L.) On blood lipids, blood sugar and platelet aggregation in patients with coronary artery disease," Prostaglandins, Leukotrienes, and Essential Fatty Acids May 1997; 56(5): 379-84.

Wang et al., "Studies on chemical constituents of the stems and leaves of *Trigonella foenum-graecum* L," Zhongguo Zhongyao Zazhi 1997; 22(8): 486-7.

Sauvaire et al., "Steroid saponins from fenugreek and some of their biological properties," Advances in Experimental Medicine and Biology 1996; 405: 37-46.

Rao et al., "Short term nutritional and safety evaluation of fenugreek," Nutrition Research 1996; 16(9): 1495-1505.

Ali Liaquat et al.,"Characterization of the Hypoglycemic Effects of *Trigonella foenum gracecum* Seed," Planta Medica 1995; 61: 358-60.

Khosla et al.,"Effect of *Trigonella foenum graecum* (Fenugreek) on blood glucose in normal and diabetic rats," Indian Journal of Physiology and Pharmacology Apr. 1995; 39(2): 173-4.

Petit et al., "Steroid saponins from fenugreek seeds: extraction, purification, and pharmacological investigation on feeding behavior and plasma cholesterol," Steroids Oct. 1995; 60(10): 674-80.

Pavithran K., "Fenugreek in diabetes mellitus," The Journal of the Association of Physicians of India Jul. 1994; 42(7): 584.

Petit et al., "Effects of a fenugreek seed extract on feeding behavior in the rat: metabolic-endocrine correlates," Pharmacology, Biochemistry, and Behavior Jun. 1993; 45(2): 369-74.

Sauvaire et al., "Implication of steroid saponins and sapogenins in the hypocholesterolemic effect of fenugreek," Lipids Mar. 1991; 26(3): 191-7.

Sharma et al., "Effect of fenugreek seeds on blood glucose and serum lipids in type I diabetes," European Journal of Clinical Nutrition Apr. 1990; 44(4): 301-6.

Swanston-Flatt et al.,"Glycaemic effects of traditional European plant treatments for diabetes. Studies in normal and streptozotocin diabetic mice," Diabetes Research Feb. 1989; 10(2): 69-73.

Alcock et al., "Stereochemistry of the 4-hydroxyisoleucine from *Trigonella foenum-graecum*," Phytochemistry 1989; 28(7): 1835-41.

Riyad et al.,"Effect of fenugreek and lupine seeds on the development of experimental diabetes in rats," Planta Medica Aug. 1988; 54(4): 286-90.

Madar et al., "Glucose-lowering effect of fenugreek in non-insulin dependent diabetics," European Journal of Clinical Nutrition Jan. 1988; 42(1): 51-4.

Madar et al., "Dietary fiber," Progress in Food & Nutrition Science 1987; 11(2): 153-74.

Madar Z, "New sources of dietary fibre," International Journal of Obesity 1987; 11 Suppl 1: 57-65.

Ribes et al., "Antidiabetic effects of subfractions from fenugreek seeds in diabetic dogs," Proceedings for the Society for Experimental Biology and Medicine Jun. 1986; 182(2): 159-66.

Ribes et al., "Effects of fenugreek seeds on endocrine pancreatic secretions in dogs," Annals of Nutrition & Metabolism 1984; 28(1): 37-43.

Valette et al., "Hypocholesterolaemic effect of fenugreek seeds in dogs," Atherosclerosis Jan. 1984; 50(1): 105-11.

Suavaire et al., "Changes in growth, proteins and free amino acids of developing seed and pod of fenugreek," Phytochemistry 1984; 23(3): 479-486.

Harman et al., "The occurrence of 4-hydroxyisoleucine in steroidal sapogenin-yielding plants," Phytochemistry 1976; 15(2): 325.

Fowden L, et al., "4-hydroxyisoleucine from Seed of *Trigonella foenum-graecum*," Phytochemistry 1973; 12: 1707-11.

Dawidar et al., "Steroid sapogenin constituents of fenugreek seeds," Planta Medica Dec. 1973; 24(4): 367-70.

\* cited by examiner

METHODS FOR DERIVING, ISOLATING, AND/OR EXTRACTING AMINO ACID COMPOSITIONS FROM FENUGREEK SEED

RELATED APPLICATIONS

This application claims the benefit of U.S. Provisional Patent Application Ser. No. 60/549,182, filed Mar. 2, 2004, and entitled "METHODS FOR DERIVING, ISOLATING, AND/OR EXTRACTING AMINO ACID COMPOSITIONS FROM FENUGREEK SEED," U.S. Patent Application Ser. No. 60/549,305, filed Mar. 2, 2004, and entitled "METHODS FOR DERIVING, ISOLATING, AND/OR EXTRACTING BIO-ACTIVE COMPOSITIONS FROM FENUGREEK SEED.

BACKGROUND

1. Field of the Invention

This invention relates to compositions and methods for extracting and separating bio-active compounds and, more particularly, to novel compositions of bio-active compounds derived, isolated, and/or extracted from Fenugreek and methods for using said novel compositions for affecting homeostasis and metabolism in mammals, in addition to methods for manufacturing the same.

2. The Background Art

Fenugreek is one of the oldest medicinal herbs and has been found to be native to southeastern Europe, northern Africa, and western Asia, although it is widely cultivated in other parts of the world. Fenugreek is known technically as *Trigonella foenum-graecum*, a member of the family Fabaceae, and commonly referred to as Greek hay.

As appreciated by those skilled in the art, Fenugreek is a legume and typically grows between two to three feet tall with light green leaves and small white flowers. A Fenugreek seed pod may contain between ten to twenty small, flat, yellow-brown seeds. Typically, a plant seed is formed having a thick or hard outer coat called a testa and often referred to as a seed coat. The inner portion of the seed coat usually contains a plant embryo and a nutritive tissue called endosperm, which surrounds the embryo. As the Fenugreek seed embryo matures, it consumes endosperm. Fenugreek seeds often have a pungent aroma and may have a bitter taste, which is said to be similar to celery.

Fenugreek has long been used as a medicinal herb and culinary additive in both Asia and the Mediterranean. As used herein, a "bio-active compound" may be defined as any substance that has an effect on living tissue. It is believed that the seed of the Fenugreek plant contains many active compounds with pharmaceutical applications such as, for example, iron, vitamin A, vitamin B, vitamin C, phosphates, flavonoids, saponins, trigonelline, and other alkaloids. Fenugreek may be taken as a stomach tonic and as a treatment for abdominal ailments. Western scientific research has provided insight into the chemical analysis of Fenugreek seeds, together with the extraction of 4-hydroxyisoleucine from Fenugreek seeds, and has, accordingly, suggested some clinical utilities of Fenugreek.

Sir L. Fowden conducted research into the analysis of Fenugreek. He taught the isolation and purification of 4-hydroxyisoleucine from Fenugreek and claimed that it is the principal unbound amino acid contained in the Fenugreek seed. In addition to 4-hydroxyisoleucine, Fowden found that Fenugreek also contains gamma-aminobutyrate, ammonia, lysine, histidine, arginine, and at least four (4) additional unidentified compounds. (See, Fowden et al, Phytochemistry, 12:1707, (1973).) Further investigation of the prior art suggests that the amino acids found in Fenugreek seeds may have some nutritional value. (See, Sauvaire et al, Nutr Rep Int, 14:527 (1976).)

Spectrophotometry methods have also been taught by those skilled in the art in the analysis of steroid sapogenin content of Fenugreek seeds and such prior art methods may be generally used in an effort to determine the composition of subfractions of defatted Fenugreek. (See, Baccou et al, Analyst, 102:458 (1977); Ribes et al, Proc Soc Exp Biol Med, 182:159 (1986).) In addition, those skilled in the art have used chloroform in an effort to extract 4-hydroxyisoleucine from Fenugreek seeds. (See, Alcock et al, Phytochemistry, 28(7): 1835 (1989).) It has been found, however, that chloroform is toxic and generally unacceptable as an extraction method under standards established by the food and drug industry.

Studies have also shown that the natural analogue of 4-hydroxyisoleucine is more effective as an antidiabetic agent than a synthetic version. There is, therefore, a suggestion that the therapeutic effects of 4-hydroxyisoleucine are best obtained from extracts of the Fenugreek seed. However, using Fenugreek seeds as a raw material source for a nutritional supplement presents some difficulties. For example, one such difficulty or disadvantage stems from the fact that a large dose of Fenugreek seeds is usually needed in order to obtain therapeutic and other nutritional effects. Patients or consumers are often unwilling to incorporate even de-fatted and de-bitterized seeds into their diet. As readily appreciated, mild gastrointestinal upset may occur at higher doses with non-defatted seeds. In addition, due to the high fiber content of Fenugreek seeds, prolonged and high dosage amounts may result in adverse side effects such as flatus or diarrhea.

The binding capabilities of the fiber in Fenugreek seeds may also affect nutrient availability, particularly of minerals. As appreciated, external application of Fenugreek seed may result in undesirable skin reactions. Thus, it would be an advancement in the art to provide a method for obtaining bio-active and therapeutic compounds from Fenugreek seeds, such that undesirable side effects resulting from ingesting the seed or portions thereof can be avoided.

During the research investigations described herein, those skilled in the art developed crude methods for extracting 4-hydroxyisoleucine from Fenugreek seeds. These prior art methods and extraction techniques have primarily focused on obtaining a "high-purity" extract of 4-hydroxyisoleucine. For example, the extraction of 4-hydroxyisoleucine using adsorption chromatography is known in the art. Such prior art methods, however, tend to yield only small quantities of 4-hydroxyisoleucine and are typically only suitable for small scale laboratory use. As previously described, an alternative extraction method exercised by those skilled in the art uses a toxic organic solvent, such as chloroform, to extract 4-hydroxyisoleucine from Fenugreek seeds, whereby contemplating inherent disadvantages to the consumer.

As indicated above, other compounds have also been isolated from Fenugreek seeds. In addition to the major isomers (2S,3R,4S)-4-hydroxyisoleucine, minor isomers 4-hydroxyisoleucine, and amino acids (including, lysine, histidine, and arginine) have been isolated. Later studies have confirmed the presence of 4-hydroxyisoleucine in Fenugreek seeds in two diastereoisomers: the major one being the (2S,3R,4S) configuration, representing about ninety percent (90%) of the total content of 4-hydroxyisoleucine, and the minor one being the (2R,3R,4S) configuration. (See, Alcock, Phytochemistry, 28:1835 (1989).)

As appreciated by those skilled in the art, the major isomer (2S,3R,4S) is presently interesting with respect to experimental evidence indicating its ability to stimulate glucose-induced insulin secretion in micromolar concentrations through a direct effect on pancreatic beta cell stimulation in a glucose dependent manner. Moreover, 4-hydroxyisoleucine is able to interact and induce additive insulinotropic effects (i.e., stimulating or affecting the production and activity of insulin, only in the presence of supranormal glucose concentrations). (See, Sauvaire et al, Diabetes, 47:206 (1998).)

Investigation of the prior art also discloses clinical studies to investigate the use of subfractions of Fenugreek in conditions of hyperglycemia, glucosuria, and hyperlipidemia which have been performed on rats, dogs, and human pancreatic tissue. (See, Shani et al, Arch Intern Pharmacodyn Ther, 210:27 (1974); Ribes et al, Ann Nutr Metab, 28: 37 (1984); Valette et al, Atherslcerosis, 50:105 (1984); Madar, Nutr Rep Int, 29:1267 (1984).)

As appreciated by those skilled in the art, clinical studies directed to conditions of hyperglycemia, as well as other conditions involving the metabolism of carbohydrates, have only investigated 4-hydroxyisoleucine as an effector of insulin-mediated or insulin-dependent pathways. The available prior art do not teach or suggest, however, Fenugreek and/or 4-hydroxyisoleucine compositions which may work synergistically or independently from insulin or insulin-mediated pathways. More particularly, there are no known prior art teachings or suggestions that 4-hydroxyisoleucine may affect the body by an insulin-independent mechanism. Stimulation of non-insulin mediated pathways may be desirous for targeting the utilization of carbohydrates in certain organ systems, (e.g., muscles, liver, etc.). Likewise, it may be desirous to avoid the general and/or systemic effects that may occur by stimulating the pancreas to produce and secrete insulin.

In addition, clinical studies conducted on Fenugreek have focused on investigating a specific subfraction of the Fenugreek seed (e.g., testa and endosperm) or, in the alternative, have focused on the specific effect of 4-hydroxyisoleucine in animals and humans with diabetes or a cholesterol disorder. Prior art directed to investigations of Fenugreek seed subfractions have failed to disclose or teach specific useful compositions.

Moreover, little or no attention has been given to the value of other bio-active compounds (e.g., free amino acids) present in Fenugreek seeds, especially in augmenting the hypoglycemic and hypercholesterolemic actions of 4-hydroxyisoleucine. At least one prior art teaches there is little or no additional utility to be gained by extracting anything other than 4-hydroxyisoleucine from Fenugreek seeds. Therefore, and as readily appreciated by those skilled in the art, a safer and more commercially practicable method for extracting compositions containing 4-hydroxyisoleucine and other bio-active components from Fenugreek is therefore needed. In addition, and as readily appreciated by those skilled in the art, novel compositions containing 4-hydroxyisoleucine for affecting the body by an insulin-independent mechanism are also needed.

BRIEF SUMMARY AND OBJECTS OF THE INVENTION

A primary object of the present invention is to provide novel compositions containing 4-hydroxyisoleucine and other bio-active compounds and methods for their extraction and separation from Fenugreek.

It is another object of the present invention to provide novel compositions of bio-active compounds and methods for their extraction and separation from Fenugreek seeds that provides 4-hydroxyisoleucine and one or more compounds selected from amino acids, alkaloids, glycosides, volatile oils, saponins, sapogenins, mannans, flavonoids, fatty acids, vitamins and provitamins, minerals, and carbohydrates.

It is also an object of the present invention to provide novel compositions of bio-active compounds and methods for their extraction and separation from Fenugreek seeds that provides 4-hydroxyisoleucine and one or more amino acids wherein a side chain has a functional group selected from acid, aliphatic, hydroxyl, base, aromatic ring, and sulfur.

It is a further object of the present invention to provide novel compositions of bio-active compounds and methods for their extraction and separation from Fenugreek seeds that provides 4-hydroxyisoleucine and one or more amino acids selected from alanine, arginine, aspartic acid, cysteine, gamma-aminobutyrate, glutamic acid, glycine, histidine, isoleucine, leucine, lysine, methionine, ornithine, phenylalanine, proline, serine, threonine, tryptophan, tyrosine and valine, and any chemical salts, anhydrides, or isomers thereof.

In addition, it is an object of the present invention to provide novel compositions of bio-active compounds and methods for their extraction and separation from Fenugreek seeds that provides 4-hydroxyisoleucine and one or more compounds selected from acetyl-choline, 25-alpha-spirosta-3,5-diene, 3,4,7-trimethylcoumarin, 3-hydroxy-4,5-dimethyl-2-furanone, 4-hydroxyisoleucine-lactone, 4-methyl-7-acetoxycoumarin, 7-acetoxy-4-methylcoumarin, alpha-galactosidase, alpha-mannosidase, aluminum, arabinose, arachidic-acid, behenic-acid, beta-carotene, beta-mannanan, beta-sitosterol, biotin, carpaine, choline, coumarin, cyanocobalamin, d-mannose, digalactosylmyoinositol, dihydroactinidiolide, dihydrobenzofuran, dioscin, diosgenin, elemene, endo-beta-mannanase, Fenugreekine, folacin, galactinol, galactomannan, gentianine, gitogenin, graecunin-h, graecunin-n, homoorientin, isovitexin, kaempferol, lecithin, lignin, luteolin, muurolene, myo-inositol, neotigogenin, niacin, nicotinic-acid, oleic-acid, orientin, orientin-arabinoside, p-coumaric-acid, palmitic-acid, protopectin, pyridoxine, quercetin, raffinose, riboflavin, rutin, saponin, selenine, stachyose, stearic-acid, thiamin, threonine, tigogenin, trigofoenosides, trigoforin, trigonelline, trigonellosides, trillin, verbascose, vicenin-1, vicenin-2, vitexin, vitexin-2'-o-p-coumarate, vitexin-7-glucoside, xanthophyll, yamogenin, yamogenin-3,26-biglycoside and yamogenin-tetrosides.

It is a further object of the present invention to provide novel compositions having an effective amount of 4-hydroxyisoleucine for affecting homeostasis and/or metabolism by an insulin-independent mechanism.

It is a still further object of the present invention to provide novel compositions of bio-active compounds and methods for their extraction and separation from Fenugreek seeds that contemplates preparing Fenugreek seeds, performing a preliminary extraction on the prepared Fenugreek seeds, and performing a secondary extraction on the Fenugreek seeds.

In addition, it is a object of the present invention to provide novel compositions of bio-active compounds and methods for their extraction and separation from Fenugreek seeds that contemplates preparing Fenugreek seeds by soaking and crushing them to separate the seed endosperm from the seed testa.

It is also an object of the present invention to provide novel compositions of bio-active compounds and methods for their extraction and separation from Fenugreek seeds that contemplates a preliminary extraction from Fenugreek seed endosperm and testa using a first solvent and a second solvent, concentrating a preliminary extract, cooling and settling a preliminary extract, and diluting the preliminary extract.

Additionally, it is an object of the present invention to provide novel compositions of bio-active compounds and methods for their extraction and separation from Fenugreek seeds that contemplates a secondary extraction from a diluted supernatant of a preliminary extraction, involving the steps of adjusting pH, filtrating through a cation resin ion exchange, washing, treating with ammonia, collecting acid, concentrating, removing ammonia, and drying.

It is a further object of the present invention to provide novel compositions of bio-active compounds and methods for their extraction and separation from Fenugreek seeds that contemplates a secondary extraction from a diluted supernatant of a preliminary extraction, involving the steps of filtering through a cation resin ion exchange, washing, treating with ethanol, collecting an effluent, adjusting pH, filtering again through a cation resin ion exchange, treating with ammonia, collecting acid, concentrating, removing ammonia, and drying.

It is a still further object of the present invention to provide novel compositions of bio-active compounds and methods for their extraction and separation from Fenugreek seeds that employs a method validation program for quantifying the content of bio-active compounds, which includes without limitation, the steps of providing a high performance liquid chromatography (HPLC) apparatus, providing the following reagents, methanol, acetonitrile, sodium acetate trihydrate, glacial acetic acid, tetrafuran, OPA reagent, de-ionized water, and 4-hydroxyisoleucine reference standard, preparing analytes for examination in an HPLC apparatus, which include a mobile phase step, a standard preparation step and a sample preparation step, preparing an HPLC apparatus injection gradient, performing an HPLC apparatus injection program, and observing and recording the peak spectra following the injection program.

It is also an object of the present invention to provide novel compositions of bio-active compounds and methods for their extraction and separation from Fenugreek seeds that involve an efficient number of steps and which are economical to produce.

Additionally, it is an object of the present invention to provide novel compositions of bio-active compounds and methods for their extraction and separation from Fenugreek seeds which provide a high potency extract yield.

It is a further object of the present invention to provide novel compositions of bio-active compounds and methods for their extraction and separation from Fenugreek seeds which provide a high quantity extract yield.

It is a still further object of the present invention to provide novel compositions of bio-active compounds and methods for their extraction and separation from Fenugreek seeds which provide an extract purity yield between about ten percent (10%) and about seventy percent (70%).

It is also an object of the present invention to provide novel compositions of bio-active compounds and methods for their extraction and separation from Fenugreek seeds that yield a profile of bio-active compounds including, without limitation, amino acids, proteins, and 4-hydroxyisoleucine.

Additionally, it is an object of the present invention to provide novel compositions of bio-active compounds and methods for their extraction and separation from Fenugreek seeds that include, without limitation, 4-hydroxyisoleucine, arginine, aspartate, threonine, serine, glutamate, proline, glycine, alanine, cysteine, valine, methionine, isoleucine, leucine, tryptophan, phenylalanine, ornithine, lysine, histidine, tyrosine, and gamma-aminobutyrate.

It is a further object of the present invention to provide novel compositions of bio-active compounds and methods for their extraction and separation from Fenugreek seeds that include, without limitation, 4-hydroxyisoleucine and one or more amino acids with a side chain containing an acidic functional group selected from glutamate and aspartate.

It is a still further object of the present invention to provide novel compositions of bio-active compounds and methods for their extraction and separation from Fenugreek seeds that include, without limitation, 4-hydroxyisoleucine and one or more amino acids with a side chain containing an aliphatic functional group selected from alanine, glycine, valine, isoleucine, and leucine.

It is also an object of the present invention to provide novel compositions of bio-active compounds and methods for their extraction and separation from Fenugreek seeds that include, without limitation, 4-hydroxyisoleucine and one or more amino acids having a side chain containing an hydroxyl functional group selected from serine, threonine, and tyrosine.

Additionally, it is an object of the present invention to provide novel compositions of bio-active compounds and methods for their extraction and separation from Fenugreek seeds that include, without limitation, 4-hydroxyisoleucine and one or more amino acids with a side chain containing a basic functional group selected from arginine, histidine, and lysine.

It is a further object of the present invention to provide novel compositions of bio-active compounds and methods for their extraction and separation from Fenugreek seeds including, without limitation, 4-hydroxyisoleucine and one or more amino acids with a side chain containing an aromatic functional group selected from phenylalanine, tryptophan, histidine, and tyrosine.

It is a still further object of the present invention to provide novel compositions of bio-active compounds and methods for their extraction and separation from Fenugreek seeds including, without limitation, 4-hydroxyisoleucine and one or more amino acids with a side chain containing a sulfur functional group selected from cysteine and methionine.

It is also an object of the present invention to provide novel compositions of bio-active compounds and methods for their extraction and separation from Fenugreek seeds that are anti-hyperglycemic.

Additionally, it is an object of the present invention to provide novel compositions of bio-active compounds and methods for their extraction and separation from Fenugreek seeds which are anti-hypercholesterolemic.

It is a further object of the present invention to provide novel compositions of bio-active compounds derived, isolated, and/or extracted from Fenugreek which may be delivered and/or administered using any pharmaceutical delivery form, for example and not by way of limitation, tablet, capsule, powder, granule, microgranule, pellet, soft-gel, controlled-release form, liquid, solution, elixir, syrup, suspension, emulsion, magma, gel, cream, ointment, lotion, transdermal, sublingual, ophthalmic form, nasal form, otic form, aerosol, inhalation form, spray, parenteral form (e.g., intravenous, intramuscular, subcutaneous), suppository, and the like.

It is a still further object of the present invention to provide novel compositions of bio-active compounds derived, isolated, and/or extracted from Fenugreek which may be delivered and/or administered using any nutraceutical delivery form, for example and not by way of limitation, tablet, capsule, powder, granule, microgranule, pellet, soft-gel, controlled-release form, liquid, solution, elixir, syrup, suspension, emulsion, magma, gel, cream, ointment, lotion, transdermal, sublingual, ophthalmic form, nasal form, otic form, aerosol, inhalation form, spray, parenteral form (e.g., intravenous, intramuscular, subcutaneous), suppository, and the like.

In addition, it is an object of the present invention to provide novel compositions of bio-active compounds derived, isolated, and/or extracted from Fenugreek which may be delivered and/or administered using any functional food delivery form, for example and not by way of limitation, bar, beverage, bread, cereal, cracker, egg, juice, juice drink, milk, soft cheese, mineral water, pasta, pasta sauce, probiotic drink soya product, spread, stimulation/energy beverage, yogurt, baby and/or children's food, women's product, men's product, meal replacement, and the like.

Also, it is an object of the present invention to provide novel compositions of bio-active compounds derived, isolated, and/or extracted from Fenugreek which may be used in combination with other amino acids, botanicals, herbals, nucleotides, nutraceuticals, nutrients, pharmaceuticals, proteins, vitamins, and the like.

Consistent with the foregoing objects, and in accordance with the invention as embodied and broadly described herein, one presently preferred embodiment of the present invention comprises novel compositions of bio-active compounds and methods for their extraction and separation from Fenugreek seeds. Specifically, one presently preferred embodiment of novel compositions of bio-active compounds extracted from Fenugreek seeds may comprise amino acids and proteins. More particularly, a composition of bio-active compounds of the present invention may include, for example, 4-hydroxyisoleucine and one or more amino acids selected from the group consisting of arginine, aspartate, threonine, serine, glutamate, proline, glycine, alanine, cysteine, valine, methionine, isoleucine, leucine, tryptophan, phenylalanine, ornithine, lysine, histidine, and gamma-aminobutyrate. Another presently preferred embodiment of a composition of bio-active compounds derived, isolated, and/or extracted from Fenugreek may include 4-hydroxyisoleucine and one or more compounds selected from amino acids, alkaloids, glycosides, volatile oils, saponins, sapogenins, mannans, flavonoids, fatty acids, vitamins and provitamins, minerals, and carbohydrates.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DESCRIPTIONS OF THE PREFERRED EMBODIMENTS

Figure 1:
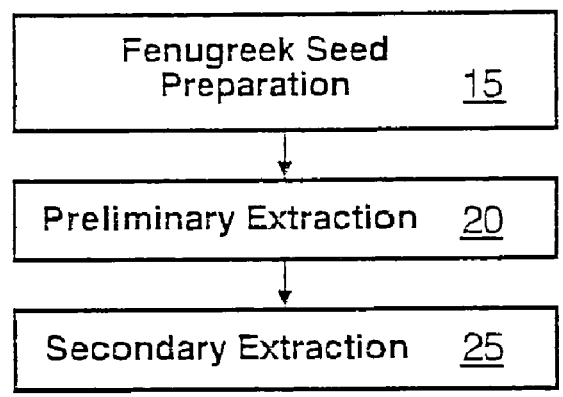
FIG. 1 is a process flow diagram illustrating one presently preferred embodiment of a method of the present invention for deriving, isolating, and/or extracting bio-active components from Fenugreek seeds comprising the steps of preparing Fenugreek seeds, performing a preliminary extraction, and performing a secondary extraction.

It will be readily understood that the components of the present invention, as generally described and illustrated in the Figures herein, could be arranged and designed in a wide variety of different configurations. Those of ordinary skill in the art will, of course, appreciate that various modifications to the details herein may be made without departing from the essential characteristics of the invention, as described. Thus, the following more detailed description of the embodiments of the compositions and methods of the present invention, as represented in FIGS. 1 through 5, is not intended to limit the scope of the invention, as claimed, but it is merely representative of the presently preferred embodiments of the invention. The presently preferred embodiments of the invention will be best understood by reference to the drawings, wherein like parts are designated by like numerals throughout.

As appreciated by those skilled in the art, "pharmacognosy" may be defined as the investigation and evaluation of natural products in the search for new drugs and bio-active compositions. An important division of pharmacognosy is "phytochemistry," which studies the chemistry of plants, plant processes and plant products. Folklore and knowledge of traditional remedies often provide the motivation for undertaking a phytochemical analysis of a particular plant or plant product. As previously described, Fenugreek may be said to fall into this condition.

Fenugreek is widely recognized to have effects on blood sugar and blood lipids, as well as many other physiological effects (e.g., expectorant, demulcent, vulnerary, anti-inflammatory, anti-spasmodic, hypotensive, emmenagogic effects (i.e., promoting menstruation), promotion of breast development, and the like). However, it was not until about thirty years ago that systematic scientific investigations of Fenugreek were initiated and subsequently, 4-hydroxyisoleucine was identified as a component of Fenugreek. "4-hydroxyisoleucine" may be classified as an amino acid compound having the following formula:

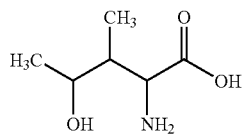

"Amino acids" may be defined as organic acids containing both an amino and carboxylic acid functional group, and which a portion of the nonacid hydrogen has been replaced by one or more amino groups. An amino acid may therefore have both basic and acidic properties. More than three hundred amino acids are known to occur in nature, however, only twenty amino acids are used in the synthesis of protein chains.

These twenty amino acids have the absolute configuration of L-glyceraldehyde and are therefore labeled as L-α amino acids. L-α amino acids include alanine, arginine, asparagine, aspartic acid (also referred to as aspartate), cysteine, glutamic acid (also referred to as glutamate), glutamine, glycine, histidine, isoleucine, leucine, lysine, methionine, phenylalanine, proline, serine, threonine, tryptophan, tyrosine, and valine.

Moreover, nine of the twenty amino acids cannot be manufactured in vivo by animals and must be supplied through the hydrolysis of dietary protein. These nine amino acids may be defined as essential amino acids and include arginine, isoleucine, leucine, lysine, methionine, phenylalanine, threonine, tryptophan, and valine.

Certain L-α amino acids have chemical and physical properties based on their respective side chains. A nonacidic hydrogen may also be replaced by a side chain with a chemical functional group. A "functional group" may be defined as an atom or group of atmos, acting as a unit, that has replaced a hydrogen atom in a hydrocarbon molecule and whose presence imparts characteristic chemical and physical properties to the hydrocarbon molecule. Characteristic chemical and physical properties may include, without limitation, acidity, basicity, aromaticity, hydrophilicity, and hydrophobicity.

Functional groups may include, without limitation, aliphatic groups, acid groups, hydroxyl groups, basic groups, aromatic groups, and sulfur groups. For example, the side chains of isoleucine, leucine, and valine all contain branched-chain aliphatic groups. These three amino acids are therefore commonly referred to as branched-chain amino acids (BCAAs). Other amino acids contain hyrdoxylic groups (e.g., serine, threonine, tyrosine), sulfur atoms (e.g., cysteine, methionine), acid groups or their amides (e.g., aspartic acid, asparagine, glutamic acid, glutamine), basic groups (e.g., arginine, lysine, histidine), aliphatic groups (e.g., alanine, glycine), and aromatic rings (histidine, phenylalanine, tyrosine, tryptophan). Proline is unique from other amino acids in that it may form an imino acid structure.

Amino acids serve many important roles in the homeostasis and physiological functions in both humans and animals. BCAA's are important to muscle growth and may account for the most common amino acids in muscle tissue. They are also important to the synthesis of neurotransmitters for the nervous system. Amino acids containing basic groups (i.e., arginine, lysine, histidine) are also important to muscle growth. These amino acids may also serve as a precursor to growth hormone and may have an important role in the transport, storage, and elimination of ammonia from the body. Glycine may be used to form porphyrins, which are used in the transport of oxygen. Glycine, aspartate, and glutamine may be used in the synthesis of purine and pyrimidine bases for use in nucleotides and management of genetic material. Arginine and glycine are important components in the synthesis of creatine, which is important for muscle function. As appreciated, tryptophan, tyrosine, and histidine may be used to form many important neurotransmitters (e.g., serotonin, melatonin, catecholamines, dopamine, and histamine).

A number of other amino acids that may have important homeostasis and physiological functions include homocysteine, homoserine, homocysteine, carnitine, ornithine, citrulline, arginosuccinic acid, 3,4-dihydroxyphenylalanine (DOPA), gamma-aminobutyric acid (GABA), glutathione, taurine, and thyroxine as well as many others. Ornithine and GABA are known to occur in Fenugreek. Trimethylhistidine is a quaternary ammonium compound that has a structure similar to the amino acid histidine and may be found in Fenugreek.

Several other bio-active compounds may also be isolated from Fenugreek, including, for example: 25-alpha-spirosta-3,5-diene, 3,4,7-trimethylcoumarin, 3-hydroxy-4,5-dimethyl-2-furanone, 4-hydroxyisoleucine-lactone, 4-methyl-7-acetoxycoumarin, 7-acetoxy-4-methylcoumarin, acetylcholine, alpha-galactosidase, alpha-mannosidase, aluminum, arabinose, arachidic-acid, behenic-acid, beta-carotene, beta-mannanan, beta-sitosterol, biotin, carpaine, choline, coumarin, cyanocobalamin, d-mannose, digalactosylmyoinositol, dihydroactinidiolide, dihydrobenzofuran, dioscin, diosgenin, elemene, endo-beta-mannanase, Fenugreekine, folacin, galactinol, galactomannan, gentianine, gitogenin, graecunin-h, graecunin-n, homoorientin, isovitexin, kaempferol, lecithin, lignin, luteolin, muurolene, myo-inositol, neotigogenin, niacin, nicotinic-acid, oleic-acid, orientin, orientin-arabinoside, p-coumaric-acid, palmitic-acid, protopectin, pyridoxine, quercetin, raffinose, riboflavin, rutin, saponin, selenine, stachyose, stearic-acid, thiamin, threonine, tigogenin, trigofoenosides, trigoforin, trigonelline, trigonellosides, trillin, verbascose, vicenin-1, vicenin-2, vitexin, vitexin-2'-o-p-coumarate, vitexin-7-glucoside, xanthophyll, yamogenin, yamogenin-3,26-biglycoside, and yamogenin-tetrosides.

Many of these other bio-active compounds are alkaloids, glycosides, volatile oils, saponins, sapogenins, galactomannans, flavonoids, fatty acids, provitamins and vitamins, minerals, and carbohydrates. "Alkaloids" may be defined as organic bases that contain nitrogen and usually contain oxygen. They are found in some seed plants and may be in the form of salts with acids (e.g., as citric, oxalic, or sulfuric acid). Alkaloids may be colorless and well crystallized and bitter tasting. They tend to be complex in structure with at least one nitrogen atom in a ring (e.g., as a pyrrole, quinoline, or indole ring), and optically and biologically active.

"Glycosides" may be defined as any of a large class of natural or synthetic compounds that are acetal derivatives of sugars. When hydrolyzed, glycosides may yield one or more molecules of a sugar and often a noncarbohydrate. Glycosides may also exist as a mixed acetal, which contains a cyclic form of a glycose, a hemiacetal, and which may be classified as a furanoside or pyranoside according to the size of the ring of the glycose or as an alpha glycoside or a beta glycoside according to the optical rotation.

"Volatile oils" may be defined as any oil which readily vaporizes when exposed to air at ordinary temperatures (i.e., room temperature). Volatile oils are sometimes referred to as essential oils. They may be any of a large class of oils of vegetable origin that impart odor and often other characteristic properties to plants. Volatile oils may be obtained from various parts of the plants (e.g., seeds, flowers, leaves, bark) by steam distillation, expression, or extraction. Typically, volatile oils are mixtures of compounds (as terpenoids, aldehydes, or esters). Volatile oils are often used in the production of perfumes, flavoring materials, and pharmaceutical preparations. Fenugreek is known to contain the following volatile oils: 3-hydroxy-4,5-dimethyl-2-furanone, dihydrobenzofuran, dihydroactinidiolide, elemene, muurolene, and selinene.

"Saponins" may be defined as any of numerous glycosides that occur in many plants, Saponins may be characterized by their properties of foaming in water solution and producing hemolysis when solutions are injected into the bloodstream. When hydrolyzed, saponins may yield a triterpenoid or steroid sapogenin and one or more sugars (e.g., glucose, galactose, xylose). As appreciated, Fenugreek may include the following saponins: 25-alpha-spirosta-3,5-diene and dioscin.

"Sapogenins" may be defined as the nonsugar portion of a saponin obtained by hydrolysis. In a few cases, sapogenins may be found free in plants. Sapogenins may be characterized by either a triterpenoid, usually pentacyclic structure (e.g., quillaic acid) or by a steroid structure usually having a spiro acetal side chain (e.g., diosgenin). Steroidal sapogenins may be useful as starting materials in the synthesis of steroidal hormones. One sapogenin, diosgenin, with the empirical formula $C_{27}H_{42}O_3$, may be obtained in Mexico from locally available yams (e.g., Mexican Wild Yam) and may be used as a starting material for the synthesis of steroid hormones (e.g., cortisone, contraceptive hormones, anabolic hormones, dehydroepiandrosterone (DHEA)). Fenugreek is known to contain the following sapogenins: diosgenin, Fenugreekine, gitogenin, neotigogenin, tigogenin and yamogenin "Galactomannans" may be defined as any of several polysaccharides that occur especially in seeds (e.g., locust beans). When hydrolyzed, galactomannan may yield galactose and mannose. Galactomannans may be characterized as soluble fiber. "Soluble fiber" may be defined as coarse, mostly indigestible plant matter, consisting primarily of polysaccharides, that when eaten stimulates intestinal peristalsis. Fiber may also be referred to as roughage, coarse fodder or bulk.

"Flavonoids" may be defined as compounds which are related to flavone, a colorless crystalline ketone $C_{15}H_{10}O_2$ or any of the derivatives of this ketone many of which (e.g., chrysin) occur as yellow plant pigments often in the form of glycosides (e.g., apiin). As appreciated, Fenugreek may contain the following flavonoids: homoorientin, orientin, quercetin, trigoforin, trillin, vicenin-1, vicenin-2, vitexin, isovitexin, and luteolin.

"Fatty acids" may be defined as any of the series of saturated aliphatic monocarboxylic acids with the general empiric formula of $C_nH_{2n+1}COOH$ (e.g., acetic acid, lauric acid, myristic acid, palmitic acid, stearic acid, arachidic acid, behenic acid, lignoceric acid), or unsaturated aliphatic monocarboxylic acids (e.g., palmitoleic acid, oleic acid, linoleic acid, arachidonic acid). Fatty acids occur naturally usually in the form of esters in fats, waxes, and oils. Fatty acids may also be in the form of glycerides in fats and fatty oils. Fatty acids, in almost all cases, contain an even number of carbon atoms most commonly between from about twelve to about twenyfour carbon atoms in the higher acids. Fatty oils may sometimes be referred to as fixed oils. These oils are generally in liquid form at ordinary temperatures.

"Vitamins" may be defined as organic compounds which are required in small quantities for normal metabolism. Vitamins cannot be synthesized by the body in adequate amounts and act typically in the regulation of various metabolic processes, but do not provide energy or serve as building units. Biochemical precursors to vitamins are often referred to as provitamins. Fenugreek may contain one or more of the following vitamins and pro-vitamins: acetylcholine, beta-carotene, choline, cyanocobalamin, folacin, niacin, nicotinic acid, pyridoxine, riboflavin, thiamine, and xanthophyll.

"Minerals" may be defined as solid homogeneous crystalline chemical elements or compounds that result from inorganic processes of nature. Minerals have a characteristic crystal structure, color, and hardness. They may exist in a chemical composition or range of compositions. Minerals may be referred to as inorganic elements, and may be essential to the nutrition of humans, animals, and plants. The following minerals may be found in Fenugreek: calcium, chromium, cobalt, copper, iron, magnesium, manganese, phosphorous, potassium, selenium, silicon, sodium, sulfur, tin, and zinc.

"Carbohydrates" may be defined as any of a group of organic compounds that includes sugars, starches, celluloses, and gums. Carbohydrates may serve as a major energy source in the diet in humans and animals. Carbohydrates may be produced by photosynthetic plants and contain only carbon (C), hydrogen (H), and oxygen (O), usually in the ratio 1:2:1, respectively.

The term "saccharide" may sometimes be used to describe a sugar. A saccharide may include any of a series of compounds consisting of carbon, hydrogen, and oxygen in which the atoms of the latter two elements, H and O, are in the ratio of 2:1, respectively, for example, $C_6H_{10}O_5$ and $C_5H_{10}O_5$. Saccharides may also be classified according to how many units or components they contain. A monosaccharide may be characterized as the simplest form of saccharide and may include those carbohydrates which cannot be hydrolyzed into a simpler form. Monosaccharides may include organic compounds with between three and nine carbon atoms. Disaccharides may be defined as compounds which, upon hydrolysis, yield two monosaccharides that may be the same or different. Oligosaccharides may be defined as compounds which, upon hydrolysis, yield between three and six monosaccharide units that may be the same or different. A polysaccharide may be defined as compounds which, upon hydrolysis, yield more than six monosaccharide units that may be the same or different.

Many of the components isolated from Fenugreek may have important functions in the homeostasis and/or intermediary metabolism of mammals. "Intermediary metabolism" may be defined as a collection of numerous biochemical pathways and processes that impact every cell and organ in the body. "Metabolic pathways" may be defined as being anabolic (i.e., involved in the synthesis of compounds constituting body structure; "building processes"), catabolic (i.e., involved in oxidative processes which release free-energy for use in other reactions and processes; "break-down processes"), and amphibiotic (i.e., involved in multiple functions and multiple processes).

Changes in homeostasis and/or intermediary metabolism may be affected by dietary intake, energetic needs (e.g., athletic performance), and in numerous disease states (e.g., diabetes, impaired glucose tolerance, impaired glucose transport, insulin resistance, impaired cholesterol transport, and metabolism (i.e., "lipid disorders")). The dietary intake of mammals may be processed through the small intestine and may be roughly divided by the liver and other areas of the body into carbohydrate, lipid, and protein components. A major component of each of these categories are glucose, triacylglycerol, and amino acids, respectively. During anabolic conditions, the body may elect to store various dietary components and conduct tissue building processes. During catabolic conditions, often in the case of athletic performance, these stores and tissues undergo significant depletion or damage. In addition, certain disease conditions may affect the ability to utilize and store dietary components.

Scientific studies conducted by the inventors of the present invention indicate that novel compositions of bio-active compounds (which may be derived, isolated, and/or extracted from Fenugreek seeds) containing 4-hydroxyisoleucine and one or more amino acids at certain concentrations, effectively enhance the transport of glucose into muscle cells in response to the presence of glucose transport factor 4 (GT-4) on muscle cells. It has been established that the behavior of cells relative to GT-4 is very strongly correlated to the behavior of a cell relative to insulin. Therefore, a supportable indication that compositions of bio-active compounds extracted from Fenugreek seeds may be used to enhance glucose transport into muscles of humans is a primary focus of the present invention.

In addition, novel compositions of bio-active (which may be derived, isolated, and/or extracted from Fenugreek seeds) containing 4-hydroxyisoleucine and an array of other amino acids may be combined with glucose or other carbohydrates to alter the physiological responses associated with a bolus administration of glucose or other carbohydrates, or produce unique physiological responses. Physiological responses may include an increase in gut absorption of glucose, stimulation of pancreatic beta cells, and enhanced disposal of glucose or other carbohydrates.

Moreover, the scientific studies conducted by the inventors of the present invention demonstrate that novel compositions of bio-active compounds in accordance with preferred embodiments of the present invention work to affect homeostasis and/or metabolism by mechanisms that are synergistic with or independent of insulin. Specifically, novel compositions of bio-active compounds of the present invention containing 4-hydroxyisoleucine may work synergistically with insulin by stimulating the pancreas to produce insulin or may promote or facilitate the function of insulin at its receptor site. In contrast, novel compositions of bio-active compounds of the present invention containing 4-hydroxyisoleucine may work independently of insulin by stimulating protein receptors on cell surfaces (e.g., glucose transport receptors) to transport glucose, carbohydrates, and/or other nutrients from outside the cell to within the cell. Therefore, novel compositions of bio-active compounds of the present invention which may be derived, isolated and/or extracted from Fenugreek may not require the presence of insulin in order to affect the body and may not require the use of biochemical and cellular pathways that are insulin-mediated.

The present invention further contemplates novel compositions containing 4-hydroxyisoleucine and other bio-active compounds and methods for their extraction and separation from Fenugreek. Presently preferred embodiments of novel compositions of the present invention may include protein, oil, ash, moisture, fiber, and one or more bio-active compounds. Presently preferred embodiments of novel compositions of the present invention may be derived, isolated, and/or extracted from *Trigonella foenum graecum*, a botanical name for Fenugreek.

One presently preferred embodiment of a composition of the present invention may include an effective amount of 4-hydroxyisoleucine in combination with one or more of the following compounds: amino acid, botanical, carbohydrate, herbal, mineral and/or electrolyte, nutraceutical, nutrient, nucleotide, pharmaceutical, protein, vitamin, and the like. Amino acids may include, for example and not by way of limitation, arginine, aspartate, threonine, serine, glutamate, glycine, alanine, cysteine, valine, methionine, isoleucine, leucine, phenylalanine, lysine, histidine, proline, tryptophan, ornithine, gamma-aminobutyrate, and tyrosine. Proteins may include, for example and not by way of limitation, growth hormone, whey protein, and casein protein. Nucleotide may include, for example and not by way of limitation, adenosine triphosphate (ATP), adenosine diphosphate (ADP), adenosine monophosphate (AMP), cyclic adenosine monophosphate (cAMP), guanosine triphosphate (GTP), guanosine diphosphate (GDP), nicotinamide adenine dinucleotide (NAD), nicotinamide adenine dinucleotide phosphate (NADP), flavin adenine dinucleotide (FAD), and the like. Vitamin may include, for example and not by way of limitation, a fat-soluble vitamin (e.g., vitamin A, vitamin D, vitamin E, vitamin K), a B-complex vitamin (e.g., vitamin B1 (thiamine), vitamin B2 (riboflavin), vitamin B3 (niacin), vitamin B5 (pantothenic acid), vitamin B6 (pyridoxine), vitamin B12 (cyanocobalamin), folic acid (sometimes referred to as vitamin B9)), vitamin C, and vitamin co-factors (e.g., biotin), and the like. Mineral and/or electrolyte may include, for example and not by way of limitation, sodium, magnesium, phosphorous, potassium, calcium, vanadium, chromium, manganese, iron, zinc, selenium, and the like. Carbohydrate may include, for example and not by way of limitation, glucose, glycogen, saccharide, sugar, and the like. Herbal and/or botanical may include, for example and not by way of limitation, ginkgo, ginseng, green tea extract, *Tribulus Terrestris* extract, *White Willow* extract, and the like.

One presently preferred embodiment of a composition of bio-active compounds of the present invention may include 4-hydroxyisoleucine and one or more compounds selected from the group consisting of amino acids, alkaloids, glycosides, volatile oils, saponins, sapogenins, mannans, flavonoids, fatty acids, vitamins and provitamins, minerals, and carbohydrates. Alkaloids, glycosides, volatile oils, saponins, sapogenins, mannans, flavonoids, fatty acids, vitamins and provitamins, minerals, and carbohydrates may be incorporated into presently preferred embodiments as follows: Alkaloids may be selected from the group consisting of carpaine, gentianine, and trigonelline. Glycosides may be selected from the group consisting of 7-acetoxy-4-methylcoumarin, coumarin, luteolin, p-coumaric-acid, rutin, trigofoenosides, trigonellosides, vitexin-2'-o-p-coumarate, yamogenin-3,26-biglycoside, and yamogenin-tetrosides. Volatile oils may be selected from the group consisting of 3-hydroxy-4,5-dimethyl-2-furanone, dihydrobenzofuran, dihydroactinidiolide, elemene, muurolene, and selinene. Saponins may be selected from the group consisting of 25-alpha-spirosta-3,5-diene and dioscin. Sapogenins may be selected from the group consisting of diosgenin, Fenugreekine, gitogenin, neotigogenin, tigogenin, and yamogenin. Mannans may be selected from the group consisting of beta-mannan and galactomannan. Flavonoids may be selected from the group consisting of homoorientin, orientin, quercetin, trigoforin, trillin, vicenin-1, vicenin-2, vitexin, isovitexin, and luteolin. Fatty acids may be selected from the group consisting of arachidic acid, behenic acid, oleic acid, palmitic acid, and stearic acid. Vitamins and provitamins may be selected from the group consisting of acetylcholine, beta-carotene, choline, cyanocobalamin, folacin, niacin, nicotinic acid, pyridoxine, riboflavin, thiamine, and xanthophyll. Minerals may be selected from the group consisting of calcium, chromium, cobalt, copper, iron, magnesium, manganese, phosphorous, potassium, selenium, silicon, sodium, sulfur, tin, and zinc. Carbohydrates may be selected from the group consisting of arabinose, d-mannose, raffinose, stachyose, and verbascose.

The present invention further contemplates novel compositions of bio-active compounds including 4-hydroxyisoleucine and one or more amino acids, wherein a side chain has a functional group selected from the group consisting of acid, aliphatic, hydroxyl, base, aromatic ring, and sulfur. Amino acids with an acid side chain functional group may be selected from the group consisting of glutamate and aspartate. Amino acids with an aliphatic side chain functional group may be selected from the group consisting of alanine, glycine, valine, isoleucine, and leucine. Amino acids with an hydroxyl side chain functional group may be selected from the group consisting of serine, threonine, and tyrosine. Amino acids with a basic side chain functional group may be selected from the group consisting of arginine, histidine, and lysine. Amino acids with an aromatic side chain functional group may be selected from the group consisting of phenylalanine, tryptophan, histidine, and tyrosine. Amino acids with a sulfur containing side chain functional group may be selected from the group consisting of cysteine and methionine.

As further contemplated herein, one presently preferred embodiment of a composition of bio-active compounds for enhancing the transport of glucose into muscle cells of the present invention may include, without limitation, an effective amount of 4-hydroxyisoleucine and one or more amino acids selected from alanine, arginine, aspartate, cysteine, gamma-aminobutyrate, glutamate, glycine, histidine, isoleucine, leucine, lysine, methionine, ornithine, phenylalanine, proline, serine, threonine, tryptophan, tyrosine, valine, and chemical salts, anhydrides or isomers thereof. Therefore, one presently preferred embodiment of a composition of bio-active compounds for enhancing the transport of glucose into muscle cells of the present invention may comprise an effective amount of 4-hydroxyisoleucine, glutamate, and aspartate. Another presently preferred embodiment of a composition of bio-active compounds for enhancing the transport of glucose into muscle cells of the present invention may include an effective amount of 4-hydroxyisoleucine, glutamate, aspartate, serine, alanine, and arginine. Still another presently preferred embodiment of a composition of bio-active compounds for enhancing the transport of glucose into muscle cells of the present invention may include an effective amount of 4-hydroxyisoleucine, glutamate, aspartate, serine, alanine, arginine, and one or more amino acids selected from the group consisting of: glycine, phenylalanine, cysteine, tryptophan, valine, and threonine. Yet another presently preferred embodiment of a composition of bio-active compounds for enhancing the transport of glucose into muscle cells of the present invention may comprise an effective amount of 4-hydroxyisoleucine, glutamate, aspartate, serine, alanine, arginine, and one or more amino acids selected from the group consisting of: glycine, phenylalanine, cysteine, tryptophan, valine, threonine, isoleucine, leucine, histidine, methionine, proline, lysine, gamma-aminobutyrate, and tyrosine.

In addition, a presently preferred embodiment of a composition of bio-active compounds for enhancing the transport of glucose into muscle cells of the present invention may include an effective amount of 4-hydroxyisoleucine, arginine, aspartate, threonine, serine, glutamate, proline, glycine, alanine, cysteine, valine, methionine, isoleucine, leucine, tryptophan, phenylalanine, lysine, histidine, ornithine, and gamma-aminobutyrate. Another presently preferred embodiment of a composition of bio-active compounds for enhancing the transport of glucose into muscle cells of the present invention may include an effective amount of 4-hydroxyisoleucine, arginine, aspartate, threonine, serine, glutamate, glycine, alanine, cysteine, valine, methionine, isoleucine, leucine, tryptophan, phenylalanine, lysine, histidine, ornithine, and gamma-aminobutyrate. In yet another presently preferred embodiment of a composition of bio-active compounds for enhancing the transport of glucose into muscle cells of the present invention may comprise an effective amount of 4-hydroxyisoleucine, glutamate, aspartate, serine, alanine, arginine, glycine, phenylalanine, cysteine, valine, and threonine, and may optionally include tryptophan.

Novel compositions according to the presently preferred embodiments of the present invention may also include a cholesterol lowering agent selected from the group consisting of probucol, clofibrate, gemfibrozil, fenofibrate, HMG CoA reductase inhibitor (e.g., atorvastatin, cerivastatin, fluvastatin, lovastatin, pravastatin, rosuvastatin, simvastatin, and chemical salts, anhydrides or isomers thereof. Additionally, presently preferred embodiments of the novel compositions of bio-active compounds of the present invention may include an herbal agent selected from flax, garlic, royal jelly, safflower, saffron, and tumeric.

One presently preferred embodiment of a method of the present invention for extracting a novel composition of bio-active compounds from Fenugreek seeds may comprise the steps of: (1) providing a plurality of Fenugreek seeds; (2) preparing the Fenugreek seeds; and (3) extracting a composition of bio-active compounds from the prepared Fenugreek seeds, wherein the composition preferably comprise 4-hydroxyisoleucine and one or more compounds selected from the group consisting of amino acids, alkaloids, glycosides, volatile oils, saponins, sapogenins, mannans, flavonoids, fatty acids, vitamins and provitamins, minerals, and carbohydrates.

One presently preferred embodiment of a method of the present invention for deriving, isolating, and/or extracting a composition of bio-active compounds from Fenugreek seeds may include the steps of: (1) soaking the Fenugreek seeds in water and (2) crushing the Fenugreek seeds. These steps of preparing the Fenugreek seeds (i.e., soaking and crushing) are intended to separate the testa portion and the endosperm portion of the Fenugreek seed. The additional steps of: (1) performing a preliminary extraction process and (2) performing a secondary extraction process are also contemplated and further disclosed herein.

In one presently preferred embodiment of a method of the present invention for deriving, isolating, and/or extracting a composition of bio-active compounds from Fenugreek seeds, a preliminary extraction process may include the steps of: (1) performing one or more extractions on the prepared Fenugreek seeds using a first solvent at a temperature from between about 20° C. and about 90° C. and for a duration of between about one hour to about three hours to yield a seed residue and a seed extract; (2) distilling the seed residue using a fractionating column by heating the seed residue until boiling, capturing, and then cooling the heated vapors derived therefrom; (3) concentrating the distilled seed residue under vacuum to separate a Fenugreek seed oil and the first solvent; (4) performing one or more extractions of the seed extract using a second solvent at a temperature from between about 20° C. and about 90° C. and for a duration of between about one hour to about three hours to yield a second seed residue and a concentrated seed extract; (5) subjecting the concentrated seed extract to a further concentration under vacuum to separate a second concentrated seed extract from the second solvent; (6) cooling the second concentrated seed extract to room temperature; (7) settling of the second concentrated seed extract into crude protein and a supernatant; and (8) diluting the supernatant with de-ionized water to a volume between about two times and about ten times the volume of the supernatant.

In one presently preferred embodiment of a method of the present invention for deriving, isolating, and/or extracting a composition of bio-active compounds from Fenugreek seeds, a secondary extraction process may include the steps of: (1) adjusting the supernatant to a pH concentration from between about one and about 6.5 by diluting with an acid to produce a pH adjusted supernatant; (2) filtering the pH adjusted supernatant through a cation ion exchange resin to remove excess cations; (3) washing the cation ion exchange resin to remove contaminants from the resin-bound pH adjusted supernatant; (4) treating the resin-bound pH adjusted supernatant with an ammonia solution; (5) collecting a secondary extraction product acidic effluent and a non-acidic effluent from the cation ion exchange resin; (6) concentrating the acidic effluent under vacuum to separate contaminants; (7) removing residual ammonia solution from the secondary extraction product; and (8) drying the secondary extraction product to obtain 4-hydroxyisoleucine and one or more amino acids.

In yet another presently preferred embodiment of a method of the present invention for deriving, isolating, and/or extracting a composition of bio-active compounds from Fenugreek seeds, a secondary extraction process may comprise the steps of: (1) filtering the supernatant through a cation ion exchange resin to remove excess cations; (2) washing the cation ion exchange resin to remove contaminants from the resin-bound supernatant; (3) treating the resin-bound supernatant with an ethanol treatment; (4) collecting a secondary extraction product acidic effluent; (5) adjusting the pH of the secondary extraction product acidic effluent from between about one and about 6.5 by diluting with an acid; (6) subjecting the pH adjusted secondary extraction product to a second filtration with a cation ion exchange resin; (7) treating the resin-bound pH adjusted secondary extraction product with an ammonia solution; (8) collecting a secondary extraction product acidic effluent and a non-acidic effluent; (9) concentrating the acidic effluent under vacuum to separate contaminants; (10) removing residual ammonia solution from the secondary extraction product; and (11) drying the secondary extraction product to obtain 4-hydroxyisoleucine and one or more amino acids.

Referring now to FIG. 1, one presently preferred embodiment of a method for deriving, isolating, and/or extracting a composition of bio-active compounds, including 4-hydroxyisoleucine and one or more other amino acids, from Fenugreek seeds of the present invention is best illustrated. Preferably, the method for deriving, isolating, and/or extracting a composition of bio-active compounds from Fenugreek seeds 10 may include the steps of: (1) preparing the Fenugreek seeds 15; (2) performing a preliminary extraction process 20; and (3) performing a secondary extraction process 25. Of course, the methods of deriving, isolating, and/or extracting a composition of bio-active compounds as taught by the present invention may include additional steps, as appreciated by those skilled in the art, in order to more optimally extract the useful bio-active compounds e.g., 4-hydroxyisoleucine and one or more amino acids) from the Fenugreek seeds.

Figure 2:
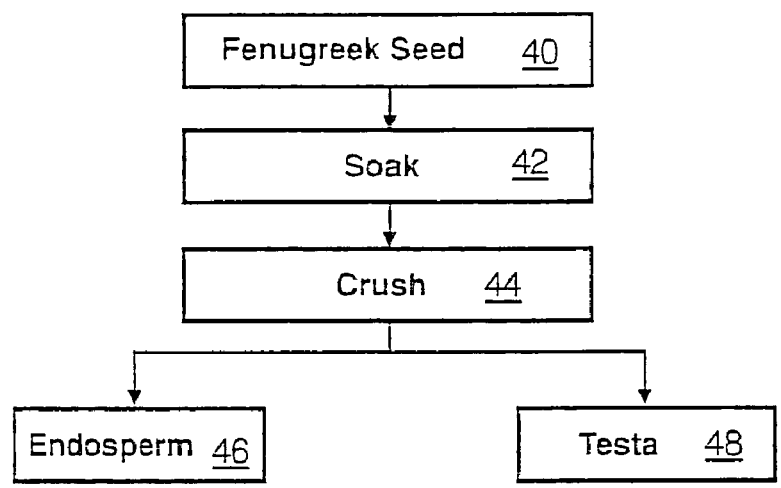
FIG. 2 is a process flow diagram illustrating one presently preferred embodiment of a method of the present invention for preparing the Fenugreek seeds as referenced in FIG. 1, comprising the steps of soaking the Fenugreek seeds in water and then crushing the soaked Fenugreek seeds.

Referring now to FIGS. 1 and 2, one presently preferred embodiment of the step for preparing the Fenugreek seeds 15 may include the steps of: (1) providing the Fenugreek seeds 40; (2) soaking the Fenugreek seeds 42; and (3) crushing the Fenugreek seeds 44. The soaking step 42 preferably involves soaking the seeds in water for a specified amount of time. As appreciated, other solutions capable of providing the preparative properties of water may also be used. After the seeds have been soaked, the step of crushing the seeds 44 is intended to effectively separate various parts of the seed. For example, the crushing step 44 may separate the thick or hard outer coat of the seed, referred to as a testa 48, from the inner portion of the seed, known as the endosperm 46. As readily known to those skilled in the art, the endosperm 46 is a nutritive tissue that surrounds the plant embryo.

Figure 3:
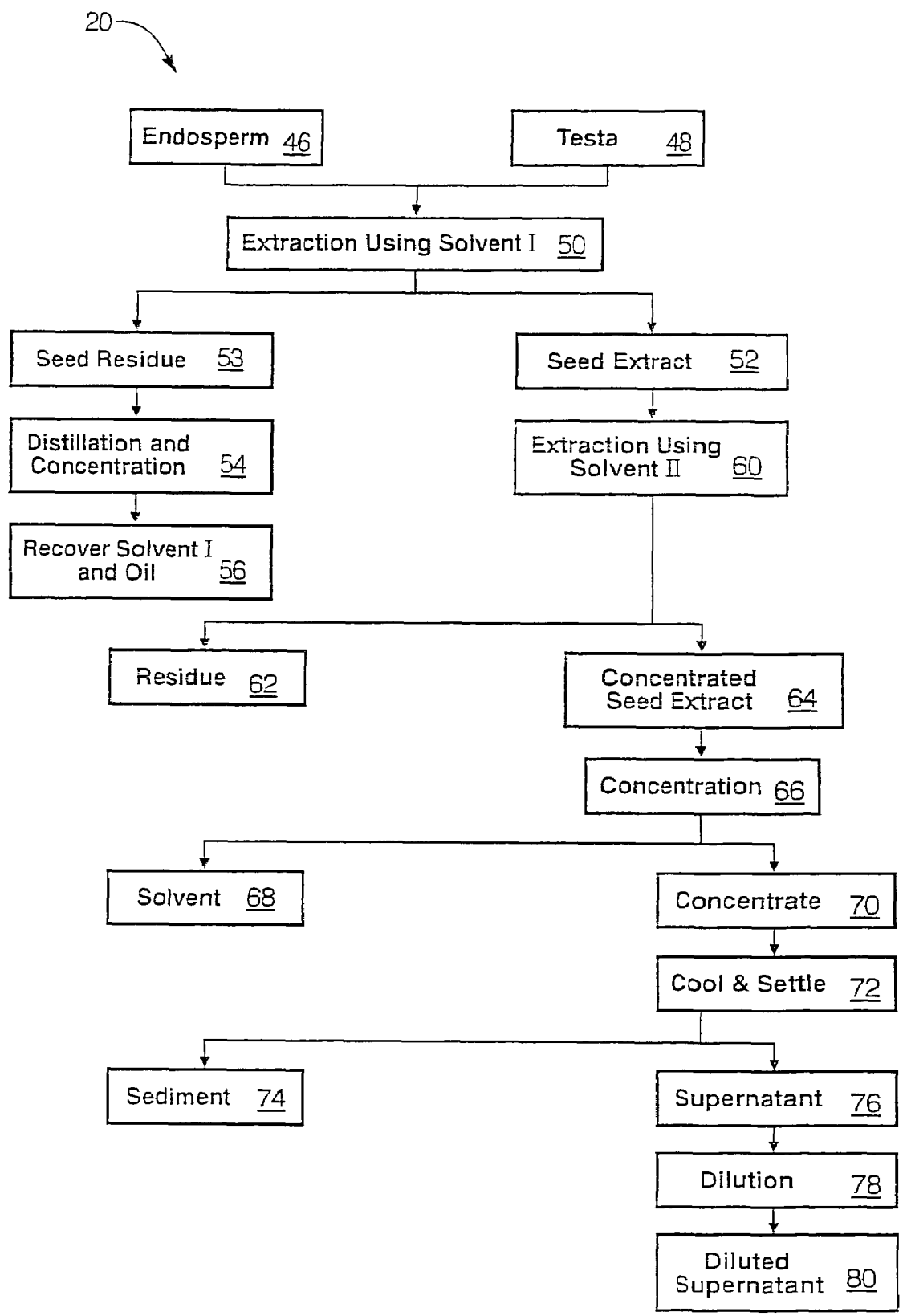
FIG. 3 is a process flow diagram illustrating one presently preferred embodiment of a method of the present invention directed to the step of preforming the preliminary extraction as referenced in FIG. 1, comprising the steps of: (1) subjecting the prepared Fenugreek seeds to a solvent I to obtain a first seed residue and seed extract; (2) subjecting the collected seed residue to a solvent II to obtain a second seed residue and a concentrated extract; (3) further concentrating under vacuum; (4) cooling and settling to obtain a sediment of crude proteins and a supernatant; and (5) diluting the supernatant with de-ionized water.

Referring specifically to FIG. 3, and generally to FIGS. 1 and 3, one presently preferred embodiment the step of performing a preliminary extraction process 20 from the endosperm 46 and the testa 48 resulting from the preparation steps 15 may include the steps of: (1) extracting 50 using a solvent (Solvent I). Solvent I may include, for example and not by way of limitation, a compound such as hexane, cyclohexane, ether, or any combinations thereof. The extraction step 50, as contemplated herein, effectively de-fats the Fenugreek seeds. Accordingly, after performing the preliminary extraction process 20, the composition of bio-active compounds resulting from the process of the present invention may be referred to as "de-fatted." The extraction step 50 may also involve repeatedly heating the combination of prepared Fenugreek seeds and Solvent I.

For example, in one presently preferred embodiment of the present invention, the combination of Fenugreek seeds and Solvent I may be heated three times to temperatures ranging from between about 20° C. and about 90° C. More preferably, the combination of seeds and Solvent I may be heated three times to temperatures ranging from between 65° C. and about 70° C. As appreciated, the combination of prepared seeds and Solvent I may be maintained at these elevated temperatures for any of a range of time periods sufficient to achieve the desired results. In one presently preferred embodiment of the present invention, the combination of prepared Fenugreek seeds and Solvent I are maintained at elevated temperatures between about one hour and about three hours. Consequently, the extraction step 50 of the present invention typically yields a seed extract 52 and a seed residue 53.

Referring specifically now to FIG. 3, a distillation and concentration step 54 may be performed on the Fenugreek seed residue 53. As appreciated, the distillation and concentration step 54 may make use of a variety of conventional means to distill and concentrate extracts from the Fenugreek seed. For example, distilling a seed residue obtained from successive extractions with a first solvent using a fractionating column may be accomplished by heating the seed residue until boiling, capturing, and then cooling the heated vapors. The distillation and concentration step 54 of one presently preferred embodiment of the preliminary extraction step 20 of the present invention may yield quantities 56 of recovered Solvent I, as well as, Fenugreek seed oil, diosgenin, Fenugreek isoflavone, Fenugreek saponin, and a soluble fiber, such as galactomannan or the like.

An extraction step 60 of one presently preferred embodiment of the preliminary extraction step 20 using a solvent (Solvent II) may be performed on the concentrated seed extract 52. Solvent II preferably comprises a solution including ethanol or a solvent having similar chemical properties to ethanol. The concentration of ethanol used in the extraction step 60 may assume a variety of values. For example, the ethanol concentration may vary between the values of between about ten percent (10%) and about ninety-five percent (95%).

In one presently preferred embodiment of the present invention, the extraction step 60 further involves the step of repeatedly heating the combination of seed extract 52 and Solvent II. Preferably, the combination may be heated three times to temperatures ranging between about 20° C. and about 90° C. More preferably, the combination of seed extract 52 and Solvent II may be heated three times to temperatures ranging between about 65° C. and about 70° C. The combination of seed extract 52 and Solvent II may be maintained at these elevated temperatures for a broad range of time periods sufficient to achieve the desired results. For example, the combination of seed extract 52 and Solvent II may be maintained at elevated temperatures between about one hour and about three hours. Further to the process disclosed herein, one presently preferred embodiment of the extraction step 60 of the present invention typically yields a seed residue 62 and a concentrated seed extract 64.

Additional steps associated with one presently preferred embodiment of a preliminary extraction process 20 may include a concentration step 66 performed on the concentrated seed extract 64. The concentration step 66 preferably comprises the use of a vacuum to separate quantities of solvent 68 and a concentrate 70. The separated concentrate 70 may then be subject to a step of cooling and settling 72 to yield a sediment 74, including crude proteins, and a supernatant 76. A dilution step 78 may then be applied to the supernatant 76 to produce a diluted supernatant 80. As appreciated, the dilution step 78 may involve the addition of de-ionized water. The volume of water added may vary. For example, the amount of water added in the dilution step 78 of one presently preferred embodiment of the present invention may include between about two to about ten times the volume of the supernatant 76. After dilution, the diluted supernatant 80 may then undergo a secondary extraction process 25, as described in FIGS. 1, 4, and 5.

It will be apparent that a variety of other methods or steps of the preliminary extraction process 20 may be performed in accordance with the inventive principles set forth herein and which are consistent with the spirit and scope of the present invention. It is intended, therefore, that the examples provided herein be viewed as exemplary of the principles of the present invention, and not as restrictive to any particular method, technique, step or ordering of steps for implementing those principles.

Figure 4:
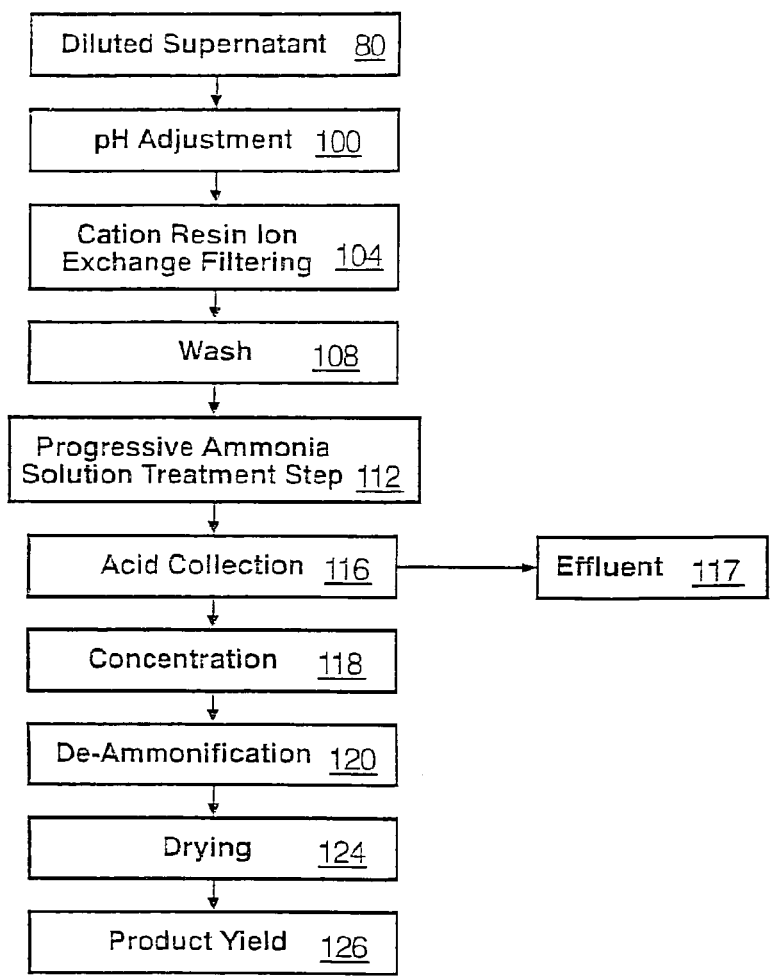
FIG. 4 is a process flow diagram illustrating one presently preferred embodiment of a method of the present invention directed to the step of performing the secondary extraction as referenced in FIG. 1, comprising the steps of: (1) resin filtration with a macropore, non-polar or weakly polar cation ion exchange resin; (2) washing with de-ionized water; (3) progressive ethanol treatment using 10%-90% ethanol; (4) effluent collection; (5) pH adjustment to 1-6.5 with six (6) Normal (N) hydrochloric acid (HCl); (6) treatment with 0.1-1 N ammonia solution; (7) effluent collection; (8) concentration under vacuum; (9) diluting with de-ionized water; (10) de-ammonification; and (11) drying to yield a composition of bio-active compounds containing an array of amino acids including between from about twenty percent (20%) to about forty percent (40%) total protein and between from about ten percent (10%) to about seventy percent (70%) 4-hydroxyisoleucine.

Referring now to FIGS. 1 and 4, the diluted supernatant 80 produced as a result of the preliminary extraction process 20 of one presently preferred embodiment of the present invention preferably undergoes a secondary extraction process 25. The secondary extraction step 25 may include the step of adjusting the pH 100 of the diluted supernatant 80. The step of adjusting the pH of the diluted supernatant 100 may include the use of a variety of solutions. For purposes of example, and not by way of limitation, hydrochloric acid may be used. The concentration of ingredients of the pH adjusting solution may have a variety of values. As appreciated, the pH of the diluted supernatant 80 may be adjusted to any of a range of values sufficient to accommodate the desired results. Accordingly, in one presently preferred embodiment of the present invention, the solution of hydrochloric acid may facilitate an adjustment in the pH of the diluted supernatant 80 to a pH in a range of between about 1 and about 6.5.

The pH adjusted, diluted supernatant 80 may then undergo a cation ion exchange resin filtering step 104. In one presently preferred embodiment, the filtering step 104 involves running the pH adjusted supernatant 80 through a resin. The cation ion exchange resin is typically macroporous and may be weakly polar or non-polar. The treated resin may then undergo a washing step 108 which may include washing the resin with water. The resin may also undergo a progressive ammonia solution treatment step 112, after which an acid collection step 116 may occur. The step of progressive ammonia treatment 112 may contemplate the use of a variety of ammonia solutions. In one presently preferred embodiment of the present invention, the ammonia solution comprises ammonium water or the like. As appreciated, the concentration of ingredients of the solution may have a variety of values. For example, the concentration of ammonium water may fall within a range of between about 0.1 N and about 1 N, and preferably to about 0.3 N.

As contemplated herein, the non-acidic effluent 117 of the progressive ammonia solution treatment step 112 may be saved and used for the isolation of nutrients having bio-activity, such as diosgenin, saponins, flavonoids, and soluble fiber, such as galactomannan and the like. Following the acid collection step 116, a concentration step 118 is preferably performed on the acidic portion. As will be appreciated, the concentration step 118 may include using a vacuum.

A de-ammonification step 120 may be incorporated in one presently preferred embodiment of the secondary extraction process 25 of the present invention to substantially remove ammonia added during previous steps of the Fenugreek seed preparation process 10. As appreciated by those skilled in the art, the de-ammonification step 120 may be accomplished by any number of conventional methods. One such method may utilize a macroporous, non-polar column, such as an HDP 100 column. Following the completion of the de-ammonification step 120, a composition of bio-active compounds extracted from the Fenugreek seed preparation, which contains 4-hydroxyisoleucine and an array of other amino acids, may be referred to as a debitterized extract.

After de-ammonification, a drying step 124 may be utilized to yield a final product 126 having useful compounds. As appreciated by those skilled in the art, the drying step 124 may utilize any number of methods, for example, spray drying, freeze drying, or drying under vacuum. Typically, the composition of bio-active compounds derived from the prepared Fenugreek seeds of the present invention (e.g., product yield 126) includes both proteins and amino acids. 4-Hydroxyisoleucine is one of such amino acids. More particularly, the product yield 126 preferably includes a composition of bio-active compounds derived from Fenugreek seeds containing 4-hydroxyisoleucine in proportions of between about ten percent (10%) and about seventy percent (70%) and between about twenty percent (20%) and about forty percent (40%) other proteins in an array of other amino acids. It is therefore possible that a composition of bio-active compounds derived from Fenugreek seeds may contain amino acids in proportions of between about ten percent (10%) and about ninety percent (90%).

It will be appreciated that a variety of other methods or steps of the secondary extraction process 25 of one presently preferred embodiment of the present invention may be performed in accordance with the inventive principles set forth herein and which are consistent with the spirit and scope of the present invention. It is intended, therefore, that the examples provided herein be viewed as exemplary of the principles of the present invention, and not as restrictive to any particular method, technique, step, or ordering of steps for implementing those principles.

Figure 5:
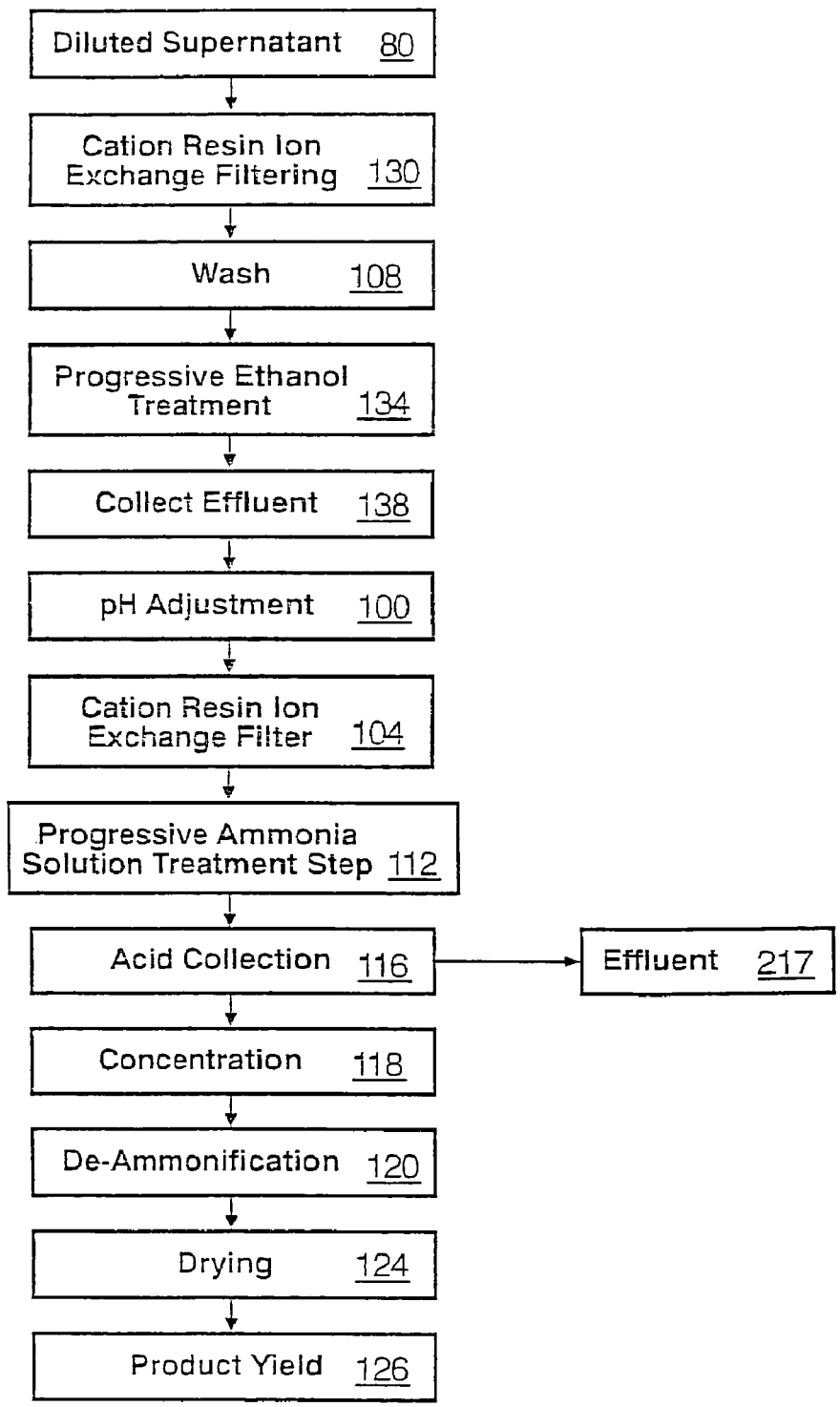
FIG. 5 is a process flow diagram illustrating an alternative presently preferred embodiment of a method of the present invention directed to the step of the secondary extraction as referenced in FIG. 1, comprising the steps of: (1) pH adjustment to about 1-6.5 with six (6) NHCl; (2) resin filtration with a macropore, non-polar or weakly polar cation ion exchange resin; (3) wash with de-ionized water; (4) treatment with about 0.05 to 2 N ammonia solution; (5) collection of effluent and acidic portion; (6) concentration of the acidic portion under vacuum; (7) de-ammonification; and (8) drying to yield a composition of bio-active compounds containing an array of amino acids including between from about twenty percent (20%) to about forty percent (40%) total protein and between from about ten percent (10%) to about seventy percent (70%) 4-hydroxyisoleucine.

Referring now to FIGS. 1 and 5, an alternative presently preferred embodiment of a secondary extraction process 125 of the present invention is illustrated. Specifically, the diluted supernatant 80 produced as a result of the preliminary extraction process 20 preferably undergoes the secondary extraction process 125. In one presently preferred embodiment of the present invention, the secondary extraction step 125 may include a cation ion exchange resin filtering step 130. The filtering step 130 contemplates running the diluted supernatant 80 over or through a resin. The resin is preferably formed having a suitable configuration and is macroporous and either weakly polar or non-polar. The treated resin may then undergo a washing step 108 which may include washing the resin with water.

The resin may also undergo a progressive ethanol treatment step 134. The step of treating the resin with ethanol 134 may involve repeatedly running solvent solutions over the resin. The concentration of ethanol in the solvent is typically increased with each run. As appreciated by those skilled in the art, the step of progressive ethanol treatment 134 may contemplate the use of a variety of suitable solutions. For example, ethanol or a solvent having similar applications in bio-active component extraction may be used.

An acid collection step 138 may immediately follow any of the runs of the progressive ethanol treatment step 134 in order to recover nutrients having bio-activity, such as saponins and flavonoids. Typically, the collected effluent 138 of the last run makes use of the highest concentration of solvent and is collected for further processing in accordance with the inventive principles of the present invention.

The effluent 138 may also undergo a pH adjustment step 100. The step of adjusting the pH 100 of the effluent 138 may include the use of a variety of solutions. For example, and not by way of limitation, hydrochloric acid may be used. The concentration of ingredients of the pH adjusting solution may have a variety of values. As appreciated, the pH of the collected effluent 138 may be adjusted to any of a range of values sufficient to accomplish the desired results. Accordingly, the solution of hydrochloric acid may facilitate an adjustment in the pH of the effluent 138 to a pH in a range of between about 1 and about 6.5.

The pH adjusted solution may then undergo a cation ion exchange resin filtering step 104. In one presently preferred embodiment of the present invention, the filtering step 104 involves running the pH adjusted solution over or through a cation ion exchange resin having ion exchange properties. The resin is preferably macroporous and may be weakly polar or non-polar. The treated resin may also undergo a progressive ammonia solution treatment step 112, after which an acid collection step 116 may occur. The step of progressive ammonia treatment 112 may contemplate the use of a variety of ammonia solutions. In one presently preferred embodiment, the ammonia solution comprises ammonium water or the like. As appreciated, the concentration of ingredients of the solution may have a variety of values. For example, the concentration of ammonium water may fall within a range of between about 0.1 N to about 1 N, and preferably to about 0.3 N.

As contemplated herein, the non-acidic effluent 217 of the progressive ammonia solution treatment step 112 may be saved and used for the isolation of nutrients having bio-activity, such as diosgenin, saponins, sapogenins, alkaloids, glycosides, volatile oils, vitamins and pro-vitamins, minerals, fatty acids, flavonoids, and soluble fiber, such as galactomannan and the like. Following the acid collection step 116, a concentration step 118 is preferably performed on the acidic portion. As will be appreciated, the concentration step 118 may include using a vacuum.

In one presently preferred embodiment of the secondary extraction process 125 of the present invention, a de-ammonification step 120 may be incorporated to substantially remove ammonia added during previous steps of the Fenugreek seed preparation process 10. As appreciated, the de-ammonification step 120 may be accomplished by any number of conventional methods. One preferred de-ammonificaiton step 120 may utilize a macroporous, non-polar column, such as an HDP 100 column. Following the completion of the de-ammonification step 120, a composition of bio-active compounds extracted from the Fenugreek seed preparation, which contains 4-hydroxyisoleucine and an array of other amino acids, may be referred to as a debitterized extract.

After de-ammonification, a drying step 124 may be utilized to yield a final product 126 having useful compounds. As appreciated by those skilled in the art, the drying step 124 may utilize any number of conventional methods, for example, spray drying, freeze drying, or drying under vacuum. Typically, the composition of bio-active compounds derived from the prepared Fenugreek seeds (e.g., product yield 126) includes both proteins and amino acids. 4-Hydroxyisoleucine is one of such amino acids. More particularly, the product yield 126 preferably includes a composition of bio-active compounds derived from Fenugreek seeds including 4-hydroxyisoleucine in proportions of between about ten percent (10%) and about seventy percent (70%) and between about twenty percent (20%) and about forty percent (40%) other proteins in an array of one or more amino acids.

It will be appreciated that a variety of other methods or steps of the secondary extraction process 125 of one presently preferred embodiment of the present invention may be performed in accordance with the inventive principles set forth herein and which are consistent with the spirit and scope of the present invention, if desired. It is intended, therefore, that the examples provided herein be viewed as exemplary of the principles of the present invention, and not as restrictive to any particular method, technique, step, or ordering of steps for implementing those principles.

In another presently preferred embodiment of the present invention, a methods validation program may be utilized to quantify the amino acid and protein content of the novel compositions of bio-active compounds of the present invention. Determination of the ratio of 4-hydroxyisoleucine and other bio-active compounds in Fenugreek may be performed using a high performance liquid chromatography (HPLC) apparatus. As contemplated herein, an HPLC apparatus including a fluorescence detector and programmable autosampler may be utilized in a methods validation program. The chromatography column may be a Zorbax stable bond SB-C18 (4.6*150 mm, 5 µm). In addition, an HPLC apparatus may include an analytical balance, accurate to 0.1 mg, an ultrasonic bath, a volumetric flask, a two liter vacuum filtration glassware with 0.2 µm membrane, variable volumetric pipets, and a magnetic stirrer and stir bars.

The reagents of a methods validation program of one presently preferred embodiment may include, for example: (1) methanol (HPLC grade), (2) acetonitrile (HPLC grade), (3) sodium acetate trihydrate (AR grade), (4) triethylamine (AR grade), (5) glacial acetic acid (AR grade), (6) tetrafuran (AR grade), (7) OPA reagent (Agilent Co. Part No. 5061-3335, containing o-phthaldialdehyde and 3-mercaptopropionic acid in borate buffer), (8) a reference standard of 4-hydroxyisoleucine (obtained from British Agricultural Lab), and (9) de-ionized water.

One presently preferred embodiment of a methods validation program of the present invention may include a mobile phase step, a standard preparation step, and a sample preparation step. In the mobile phase step, buffer A, buffer B, and a filter/degas step may be utilized. Buffer A may be prepared in a one-liter beaker, wherein 1.36 g of sodium acetate trihydrate may be dissolved in 500 mL water. This combination may be stirred until thoroughly dissolved. 90 µL of triethylamine may be added and mixed. The pH may be adjusted to about 7.2 with between about one percent (1%) and about two percent (2%) of acetic acid solution. 1.5 mL of tetrafuran may then be added and mixed. The final mixture may be labeled—"buffer A."

Buffer B may be formed, in one presently preferred embodiment, in accordance with the following procedure. In a beaker, 1.36 g sodium acetate trihydrate may be dissolved in 100 mL of water. This combination may be stirred until thoroughly dissolved. The pH may be adjusted to about 7.2 with between about one percent (1%) and about two percent (2%) acetic acid solution. 200 mL of methanol and 200 mL of acetonitrile may then be added to the beaker and mixed well. The final mixture may be labeled—"buffer B." Preferably, the buffers may be filtered and degassed using a vacuum and 0.2 µm membrane.

In one presently preferred embodiment of the present invention, a methods validation program standard preparation step may include, accurately weighing about 10 mg of a reference compound and placing the compound into a 50 mL volumetric flask. The reference compound may be dissolved using about 30 mL deionized water and undergoing sonicate for approximately ten minutes. The flask is preferably allowed to cool to room temperature and then the solution may be diluted with water to specific concentration and mixed well. The standard preparation may then be sealed with a parafilm and stored under refrigeration until needed.

A methods validation program sample preparation step may include the steps of accurately weighing about 25 mg of a composition of bio-active compounds extracted from Fenugreek seed and dissolving with about 30 mL deionized water in a 50 mL volumetric flask and undergoing sonicate for approximately ten minutes. The flask is preferably allowed to cool to room temperature and then the solution may be diluted with water to specific concentration and mixed well. A sample preparation may be filtered prior to being injected into an HPLC apparatus, if desired.

Chromatographic conditions for one presently preferred embodiment of a methods validation program of the present invention may include, for example, a Zorbax stable bond SB-C18 column, a column temperature of about 30° C., and an EX 340 nM, EM 450 chromatographic detector. The following gradients and injection program may be utilized:

Gradient:

| Time (min) | % A | % B | F (mL/min) |
|---|---|---|---|
| 0.00 | 100 | 0 | 1.0 |
| 17.0 | 50 | 50 | 1.0 |
| 20.0 | 0 | 100 | 1.0 |
| 20.1 | 0 | 100 | 1.0 |
| 24.0 | 100 | 0 | 1.0 |
| 35.0 | 100 | 0 | 1.0 |

Injection Program:

| Row | Action |
|---|---|
| 1 | Draw 5.0 µL from vial 1 (buffer) |
| 2 | Draw 1.0 µL from vial 2 (sample) |
| 3 | Mix 6.0 µl in air, max. speed, 6 times |

-continued

| Row | Action |
|---|---|
| 4 | Submerge injector tip in vial 11 (wash vial) |
| 5 | Draw 1.0 µL from vial 3 (OPA reagent) |
| 6 | Mix 7.0 µL in air, max. speed, 6 times |
| 7 | Submerge injector tip in vial 11 (wash vial) |
| 8 | Inject |

A methods validation program specificity may be performed by examining the spectrum of the identified peak. This peak may show the spectra of the sample and reference standards. A methods validation program linearity may be analyzed preparing standard preparations of 4-hydroxyisolucine and assayed as directed in the method validation program. One such linearity was undertaken by the inventors of the present invention and the following results were observed:

| Concentration (mg/ml) | Peak area | Response (area/conc.) |
|---|---|---|
| 0.09 | 1336.9 | 3.36600e−3 |
| 0.18 | 2654.1 | 3.39098e−3 |
| 0.27 | 4040.7 | 3.34101e−3 |
| y-intercept | −26.56667 | Ave = 3.36600e−3 |
| slope | 300.4222 | SD = 0.024985 |
| correlation | 0.99989 | RSD = 0.74% |

The correlation coefficient is satisfactory (®>0.99950) and the data demonstrates that one presently preferred embodiment of a methods validation program of the present invention has good linearity.

A methods validation program precision may be analyzed with six separated tests performed on a test sample, if desired. One such precision analysis was undertaken and the following results were observed:

| 4-OH-Ile precision LOT NO: 2060052 | | |
|---|---|---|
| Number | Peak area | Assay |
| 1 | 2827.8 | 35.4 |
| 2 | 2758.2 | 35.3 |
| 3 | 2997.0 | 34.9 |
| 4 | 2721.5 | 35.1 |
| 5 | 2510.6 | 34.9 |
| 6 | 2562.2 | 35.4 |
| Average | — | 35.2 |
| SD | — | 0.234 |
| RSD | — | 0.66% |

| 4-OH-Ile precision LOT NO: 20020402 | | |
|---|---|---|
| Number | Peak area | Assay |
| 1 | 3369.0 | 43.6 |
| 2 | 3214.2 | 43.9 |
| 3 | 3292.9 | 43.5 |
| 4 | 3112.6 | 43.0 |
| 5 | 3394.8 | 44.1 |
| 6 | 3305.2 | 43.7 |
| average | — | 43.6 |
| SD | — | 0.378 |
| RSD | — | 0.87% |

| 4-OH-Ile precision LOT NO: FSE02G31-32 | | |
|---|---|---|
| Number | Peak area | Assay |
| 1 | 3762.9 | 49.2 |
| 2 | 3574.1 | 48.2 |
| 3 | 3560.3 | 48.2 |
| 4 | 3599.4 | 48.3 |
| 5 | 3629.7 | 49.1 |
| 6 | 3627.1 | 49.1 |
| average | — | 48.7 |
| SD | — | 0.496 |
| RSD | — | 1.00% |

From these results, relative standard deviation (RSD) is less than three percent (<3%). Based on the foregoing, one presently preferred embodiment of a methods validation program of the present invention delivered good precision for the sample.

A methods validation program was conducted and analyzed for reproducibility by testing a same sample with multiple HPLC assays on consecutive days. The following results were observed:

| 4-OH-Ile reproducibility LOT NO: 2060052 | | | |
|---|---|---|---|
| Number | Day 1 | Day 2 | Over 2 days |
| 1 | 35.4 | 34.5 | |
| 2 | 35.3 | 35.7 | |
| 3 | 34.9 | 36.2 | |
| 4 | 35.1 | 34.9 | |
| 5 | 34.9 | 35.6 | |
| 6 | 35.4 | 34.6 | |
| Average | 35.2 | 35.2 | 35.2 |
| SD | 0.234 | 0.683 | 0.489 |
| RSD | 0.66% | 1.94% | 1.39% |

| 4-OH-Ile reproducibility LOT NO: 2002-0402 | | | |
|---|---|---|---|
| Number | Day1 | Day2 | Over 2 days |
| 1 | 43.6 | 44.7 | |
| 2 | 43.9 | 43.7 | |
| 3 | 43.5 | 43.9 | |
| 4 | 43.0 | 43.5 | |
| 5 | 44.1 | 43.5 | |
| 6 | 43.7 | 45.0 | |
| Average | 43.6 | 44.0 | 43.8 |
| SD | 0.378 | 0.644 | 0.548 |
| RSD | 0.87% | 1.46% | 1.25% |

The RSD is less than three percent (<3%) which shows that the methods validation program of one presently preferred embodiment of the present invention has good reproducibility.

A methods validation program was conducted and analyzed for recovery and accuracy using spiked and recovered sample analyte and spiked and recovered standard analyte. The following results were observed:

| 4-OH-Ile Recovery | | | | | |
|---|---|---|---|---|---|
| | Sample Spiked (mg) | Spiked (4-OH ILE) (mg) | Recovered (4-OH ILE) (mg) | Recovery (4-OH ILE) (%) | Average (%) |
| FSE2060052 + FSE02G31-32 | 10.8 | 5.34 | 5.23 | 98.0 | 97.9 |
| | 22.1 | 10.92 | 10.68 | 97.8 | |
| | 33.9 | 16.75 | 16.41 | 98.0 | |
| FSE20020402 + FSE02G31-32 | 10.2 | 5.04 | 4.98 | 98.7 | |
| | 21.6 | 10.67 | 10.37 | 97.2 | |
| | 30.8 | 15.22 | 14.84 | 97.6 | |

These foregoing data demonstrate that one presently preferred embodiment of the methods validation program of the present invention has good accuracy.

The following examples will illustrate the practice of the present invention in further detail. It will be readily understood by those skilled in the art that the following methods, formulations, and compositions of bio-active compounds which may be derived, isolated, and/or extracted from Fenugreek seeds to create a unique, high-potency, bio-active Fenugreek seed extract of the present invention, as generally described and illustrated in the Examples herein, are to be viewed as exemplary of the principles of the present invention, and not as restrictive to a particular structure or process for implementing those principles. Thus, the following more detailed description of the presently preferred embodiments of the methods, formulations, and compositions of the present invention, as represented in Examples I-V, is not intended to limit the scope of the invention, as claimed, but is merely representative of presently preferred embodiments of the invention.

EXAMPLE I

Based on the foregoing description and results of the methods validation program of one presently preferred embodiment of the present invention, Lot No. 2090769 was analyzed using HPLC as previously described and was found to contain a composition of bio-active compounds derived, isolated, and/or extracted from Fenugreek seeds of the present invention resulting in the following composition:

| Measurement | % (w/w) |
|---|---|
| Protein | 42.52 |
| Oil Content | 0.20 |
| Ash | 3.19 |
| Moisture | 13.10 |
| Soluble Fiber | 2.30 |
| Insoluble Fiber | 0.90 |
| Amino Acids | |
| Arginine | 1.92 |
| Aspartate | 1.94 |
| Threonine | 0.43 |
| Serine | 0.32 |
| Glutamate | 3.23 |
| Proline | 0.41 |
| Glycine | 1.03 |
| Alanine | 1.17 |
| Cysteine | 0.08 |
| Valine | 0.25 |
| Methionine | 0.29 |
| Isoleucine | 0.26 |
| Leucine | 0.28 |

| Measurement | % (w/w) |
| --- | --- |
| Tryptophan | 0.14 |
| Phenylalanine | 0.73 |
| Lysine | 0.22 |
| Histidine | 0.29 |
| Tyrosine | 0.03 |
| 4-hydroxyisoleucine | 24.50 |
| Total Amino Acids | 37.79 |

As shown above, one presently preferred embodiment of a composition of bio-active compounds consists of about 42.5% protein, about 0.2% oil, about 3.19% ash, about 13.10% moisture, about 2.30% insoluble fiber, about 0.90% soluble fiber, and about thirty-eight percent (38%) free amino acids, including about 25% 4-hydroxyisoleucine and quantities of the following amino acids: arginine, aspartate, threonine, serine, glutamate, proline, glycine, alanine, cysteine, valine, methionine, isoleucine, leucine, tryptophan, phenylalanine, lysine, histidine, and tyrosine.

Since the compositions of bio-active compounds derived, isolated, and/or extracted from Fenugreek seeds of the present invention are processed to include 4-hydroxyisoleucine and one or more amino acids, it will be readily appreciated that a composition of bio-active compounds isolated from Fenugreek seeds may contain 4-hydroxyisoleucine with one or more various amino acids as described herein. It is intended, therefore, that the present example provided hereinabove be viewed as exemplary of the principles of the present invention, and not as restrictive to a particular structure or method for implementing those principles.

EXAMPLE II

Based on the foregoing description and results of the methods validation program of one presently preferred embodiment of the present invention, Lot No. 2121492 was analyzed using HPLC as previously described and was found to contain a composition of bio-active compounds derived, isolated, and/or extracted from Fenugreek seeds resulting in the following composition:

| Measurement | % (w/w) |
| --- | --- |
| Protein | 52.43 |
| Oil Content | 0.07 |
| Ash | 1.59 |
| Moisture | 8.42 |
| Soluble Fiber | 1.80 |
| Insoluble Fiber | 0.20 |
| Amino Acids | |
| Arginine | 1.46 |
| Aspartate | 1.51 |
| Threonine | 0.34 |
| Serine | 0.12 |
| Glutamate | 3.05 |
| Proline | 0.37 |
| Glycine | 0.96 |
| Alanine | 1.31 |
| Cysteine | 0.07 |
| Valine | 0.35 |
| Methionine | 0.24 |
| Isoleucine | 0.23 |
| Leucine | 0.18 |
| Tryptophan | 0.02 |
| Phenylalanine | 0.33 |

| Measurement | % (w/w) |
| --- | --- |
| Lysine | 0.19 |
| Histidine | 0.29 |
| Tyrosine | 0.07 |
| 4-hydroxyisoleucine | 24.40 |
| Total Amino Acids | 35.49 |

As shown above, one presently preferred embodiment of a composition of bio-active compounds consists of about 52% protein, about 0.07% oil, about 1.59% ash, about 8.42% moisture, about 1.80% insoluble fiber, about 0.20% soluble fiber, and about thirty-five percent (35%) free amino acids, including about 24% 4-hydroxyisoleucine and quantities of the following amino acids: arginine, aspartate, threonine, serine, glutamate, proline, glycine, alanine, cysteine, valine, methionine, isoleucine, leucine, tryptophan, phenylalanine, lysine, histidine, and tyrosine.

histidine, and tyrosine.

Since the compositions of bio-active compounds derived, isolated, and/or extracted from Fenugreek seeds of the present invention are processed to include 4-hydroxyisoleucine and one or more amino acids, it will be readily appreciated that a composition of bio-active compounds isolated from Fenugreek seeds may contain 4-hydroxyisoleucine with one or more various amino acids as described herein. It is intended, therefore, that the present example provided hereinabove be viewed as exemplary of the principles of the present invention, and not as restrictive to a particular structure or method for implementing those principles.

EXAMPLE III

Based on the foregoing description and results of the methods validation program of one presently preferred embodiment of the present invention, Lot No. 2101114 was analyzed using HPLC as previously described and was found to contain a composition of bio-active compounds derived, isolated, and/or extracted from Fenugreek seeds resulting in the following composition:

| Measurement | % (w/w) |
| --- | --- |
| Amino Acids | |
| Arginine | 1.09 |
| Aspartate | 1.82 |
| Threonine | 0.41 |
| Serine | 1.71 |
| Glutamate | 3.09 |
| Proline | 0.20 |
| Glycine | 0.94 |
| Alanine | 1.48 |
| Cysteine | 0.79 |
| Valine | 0.46 |
| Methionine | 0.15 |
| Isoleucine | 0.21 |
| Leucine | 0.20 |
| Tryptophan | 0.81 |
| Phenylalanine | 0.73 |
| Lysine | 0.17 |
| Histidine | 0.16 |
| Ornithine | 0.06 |
| Gamma-aminobutyrate | 0.34 |
| 4-hydroxyisoleucine | 26.00 |
| Total Amino Acids | 40.82 |

As shown above, one presently preferred embodiment of a composition of bio-active compounds consists of about 41% free amino acids, including about 26% 4-hydroxy-isoleucine and quantities of the following amino acids: arginine, aspartate, threonine, serine, glutamate, proline, glycine, alanine, cysteine, valine, methionine, isoleucine, leucine, tryptophan, phenylalanine, lysine, histidine, ornithine and gamma-aminobutyrate, histidine, and tyrosine.

Since the compositions of bio-active compounds derived, isolated, and/or extracted from Fenugreek seeds of the present invention are processed to include 4-hydroxyisoleucine and one or more amino acids, it will be readily appreciated that a composition of bio-active compounds isolated from Fenugreek seeds may contain 4-hydroxyisoleucine with one or more various amino acids as described herein. It is intended, therefore, that the present example provided hereinabove be viewed as exemplary of the principles of the present invention, and not as restrictive to a particular structure or method for implementing those principles.

EXAMPLE IV

Based on the foregoing description and results of the methods validation program of one presently preferred embodiment of the present invention, Lot No. 2101055 was analyzed using HPLC as previously described and was found to contain a composition of bio-active compounds derived, isolated, and/or extracted from Fenugreek seeds resulting in the following composition:

| Measurement | % (w/w) |
| --- | --- |
| Amino Acids | |
| Arginine | 0.90 |
| Aspartate | 1.49 |
| Threonine | 0.35 |
| Serine | 4.44 |
| Glutamate | 2.47 |
| Glycine | 0.81 |
| Alanine | 1.22 |
| Cysteine | 0.67 |
| Valine | 0.41 |
| Methionine | 0.20 |
| Isoleucine | 0.20 |
| Leucine | 0.17 |
| Tryptophan | 0.69 |
| Phenylalanine | 0.61 |
| Lysine | 0.13 |
| Histidine | 0.14 |
| Ornithine | 0.04 |
| Gamma-aminobutyrate | 0.29 |
| 4-hydroxyisoleucine | 23.26 |
| Total Amino Acids | 38.49 |

As shown above, one presently preferred embodiment of a composition of bio-active compounds consists of about 39% free amino acids, including about 23% 4-hydroxy-isoleucine and quantities of the following amino acids: arginine, aspartate, threonine, serine, glutamate, glycine, alanine, cysteine, valine, methionine, isoleucine, leucine, tryptophan, phenylalanine, lysine, histidine, ornithine, and gamma-aminobutyrate.

Since the compositions of bio-active compounds derived, isolated, and/or extracted from Fenugreek seeds of the present invention are processed to include 4-hydroxyisoleucine and one or more amino acids, it will be readily appreciated that a composition of bio-active compounds isolated from Fenugreek seeds may contain 4-hydroxyisoleucine with one or more various amino acids as described herein. It is intended, therefore, that the present example provided hereinabove be viewed as exemplary of the principles of the present invention, and not as restrictive to a particular structure or method for implementing those principles.

EXAMPLE V

Based on the foregoing description and results of the methods validation program of one presently preferred embodiment of the present invention, Lot No. 2090898 was analyzed using HPLC as previously described and was found to contain a composition of bio-active compounds derived, isolated, and/or extracted from Fenugreek seeds resulting in the following composition:

| Measurement | % (w/w) |
| --- | --- |
| Amino Acids | |
| Arginine | 0.81 |
| Aspartate | 1.27 |
| Threonine | 0.23 |
| Serine | 0.87 |
| Glutamate | 1.96 |
| Glycine | 0.67 |
| Alanine | 1.17 |
| Cysteine | 0.74 |
| Valine | 0.36 |
| Methionine | 0.10 |
| Isoleucine | 0.22 |
| Leucine | 0.21 |
| Phenylalanine | 0.56 |
| Ornithine | 0.08 |
| Lysine | 0.13 |
| Histidine | 0.10 |
| Tyrosine | 0.42 |
| 4-hydroxyisoleucine | 24.11 |
| Total Amino Acids | 34.01 |

As shown above, one presently preferred embodiment of a composition of bio-active compounds consists of about 34% free amino acids, including about 24% 4-hydroxy-isoleucine and quantities of the following amino acids: arginine, aspartate, threonine, serine, glutamate, glycine, alanine, cysteine, valine, methionine, isoleucine, leucine, phenylalanine, ornithine, lysine, histidine, and tyrosine.

Since the compositions of bio-active compounds derived, isolated, and/or extracted from Fenugreek seeds of the present invention are processed to include 4-hydroxyisoleucine and one or more amino acids, it will be readily appreciated that a composition of bio-active compounds isolated from Fenugreek seeds may contain 4-hydroxyisoleucine with one or more various amino acids as described herein. It is intended, therefore, that the present example provided hereinabove be viewed as exemplary of the principles of the present invention, and not as restrictive to a particular structure or method for implementing those principles.

It is readily appreciated that the tests conducted on the presently preferred embodiments of novel compositions of bio-active compounds derived from Fenugreek seed derived, isolated, and/or extract in accordance with the presently preferred embodiments of the Fenugreek seed preparation process may be configured or modified to apply to any number of embodiments for practicing the present invention which are consistent with the spirit and scope of the present invention. It is intended, therefore, that the examples provided herein be viewed as exemplary of the principles of the present invention, and not as restrictive to a particular structure or method for implementing those principles.

In addition, it has been shown that preferred embodiments of the compositions of bio-active compounds processed in accordance with the methodologies of the present invention are helpful in restoring healthy energy balance in humans and animals. Novel compositions and methods of the compositions of bio-active compounds of the present invention that may be derived, isolated, and/or extracted from Fenugreek seeds have been found to balance blood sugar levels by helping the body make more efficient use of existing (i.e., endogenous) insulin. As appreciated, this activity may be characterized as an increase in insulin sensitivity or insulin sensitivity promoter.

Also, preferred embodiments of the compositions of bio-active compounds of the present invention that may be derived, isolated, and/or extracted from Fenugreek seeds have been found to be helpful in improving athletic performance in a human or animal. Moreover, novel compositions of bio-active compounds of the present invention have been found to decrease recovery times following conditions of muscle performance by increasing the rate of muscle glycogen resynthesis.

Furthermore, of the compositions of bio-active compounds of the present invention that may be derived, isolated, and/or extracted from Fenugreek seeds have been found to be helpful in aiding weight management efforts in a human or animal. Moreover, novel compositions of bio-active compounds of the present invention that may be derived from Fenugreek seeds have been found to reduce body fat potential by converting glucose to glycogen (i.e., "muscle fuel") instead of fat. In addition, this conversion may reduce weight and blood triglyceride gain in conditions of high-fat diet, as appreciated.

It will be further appreciated that the novel compositions of bio-active compounds of the present invention may be administered in any manner known to those of ordinary skill in the art, including but not limited to, oral, parenteral, sublingual, topical, transdermal, intramuscular, or inhalation, and may also contain excipients chosen in accordance with the dosage form adopted. Moreover, the dosage of the extract compositions given to an individual may vary on the basis of several considerations without departing from the spirit and scope of the present invention and will, accordingly, depend on the targeted individual's particular case to be treated.

From the above discussion, it will be appreciated that the present invention provides novel compositions of bio-active compounds and uses of the same, in addition to methods for derivation, isolation, and/or extraction of the bio-active compounds of the composition from Fenugreek seeds. Unlike the prior art, the present invention provides novel compositions and methods for extracting and separating bio-active compounds derived from Fenugreek seeds including, without limitation, 4-hydroxyisoleucine and one or more compounds selected from the group consisting of: amino acids, alkaloids, glycosides, volatile oils, saponins, sapogenins, mannans, flavonoids, fatty acids, vitamins and provitamins, minerals, and carbohydrates. Amino acids may include, without limitation, one of more compounds selected from the group consisting of: arginine, aspartate, threonine, serine, glutamate, proline, glycine, alanine, cysteine, valine, methionine, isoleucine, leucine, tryptophan, phenylalanine, ornithine, lysine, histidine, and gamma-aminobutyrate.

Also unlike the prior art, the present invention provides novel compositions of bio-active compounds comprising 4-hydroxyisoleucine which may be used to affect homeostasis and/or metabolism by an insulin-independent mechanism. As appreciated, an insulin-independent mechanism may mean that it does not require insulin or an insulin-mediated pathway in order to affect the body.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for obtaining an extract composition of bio-active compounds from Fenugreek seeds, the method comprising the steps of:
   providing a plurality of Fenugreek seeds;
   soaking the Fenugreek seeds in water;
   crushing the Fenugreek seeds; and
   performing a preliminary extraction on the crushed seeds to collect a crude protein and a supernatant wherein the preliminary extraction process comprises the steps of:
      performing one or more extractions on the crushed Fenugreek seeds using a first solvent at a temperature between about 20° C. and about 90° C. and for a duration of between about 1 hour and about 3 hours to yield a seed residue and a seed extract;
      distilling the seed residue using a fractionating column by heating the seed residue until boiling, capturing, and then cooling the heated vapors derived therefrom;
      concentrating the distilled seed residue under vacuum to separate a Fenugreek seed oil and the first solvent;
      performing one or more extractions of the seed extract using a second solvent at a temperature between about 20° C. and about 90° C. and for a duration of between about 1 hour and about 3 hours to yield a second seed residue and a concentrated seed extract;
      subjecting the concentrated seed extract to a further concentration under vacuum to separate a second concentrated seed extract from the second solvent;
      cooling the second concentrated seed extract to room temperature;
      settling the second concentrated seed extract into the crude protein and the supernatant; and
      diluting the supernatant with de-ionized water to a volume between about 2 and about 10 times the volume of the supernatant, and
   performing a secondary extraction on the supernatant to collect a secondary extraction product comprising an amino acid content having a total weight comprising 4-hydroxyisoleucine and glutamate, wherein the 4-hydroxyisoleucine comprises an amount between 60% and about 70% of the total weight of the amino acid content and the glutamate comprises an amount between about 6% and about 9% of the total weight of the amino acid content,
   wherein the secondary extraction process comprises the steps of:
      filtering the supernatant through a cation ion exchange resin to remove excess cations;
      washing the cation ion exchange resin to remove contaminants from the resin-bound supernatant;
      treating the resin-bound supernatant with an ethanol treatment;
      collecting a secondary extraction product acidic effluent;

adjusting the pH of the secondary extraction product acidic effluent from about 1 to about 6.5 by diluting with an acid;

subjecting the pH adjusted secondary extraction product to a second filtration with a cation ion exchange resin;

treating the resin-bound pH adjusted secondary extraction product with an ammonia solution;

collecting a secondary extraction product acidic effluent and a non-acidic effluent;

concentrating the acidic effluent under vacuum to separate contaminants;

removing residual ammonia solution from the secondary extraction product; and drying the secondary extraction product to obtain said extract composition.

2. The method as defined in claim 1, wherein the cation ion exchange resin filtering step comprises the step of introducing the pH adjusted supernatant through the cation ion exchange resin.

3. The method as defined in claim 1, wherein the washing step comprises the step of introducing water through the cation ion exchange resin.

4. The method as defined in claim 1, wherein the ethanol treatment step comprises the step of running progressively concentrated ethanol solutions through the cation ion exchange resin.

5. The method as defined in claim 1, wherein the pH adjustment step comprises the step of diluting with 6 N hydrochloric acid.

6. The method as defined in claim 1, wherein the ammonia solution treatment step comprises the step of running progressively concentrated ammonia solutions through the cation ion exchange resin.

7. The method as defined in claim 1, wherein the ammonia solution comprises ammonium water.

8. The method as defined in claim 7, wherein the ammonium water comprises a concentration of about 0.1 N to about 1 N.

9. The method as defined in claim 1, wherein the ammonium water comprises a concentration of about 0.3 N.

10. The method as defined in claim 1, wherein the drying step is selected from the group consisting of spray drying, freeze drying, and drying under vacuum.

11. The method as defined in claim 1, wherein the first solvent comprises an organic solvent.

12. The method as defined in claim 1, wherein the second solvent comprises an aqueous-alcohol mixture.

13. The method as defined in claim 12, wherein the aqueous-alcoholic mixture is between about 10% and about 95% ethanol.

14. A method of preparing a pharmaceutical delivery form comprising obtaining an extract composition of bioactive compounds from Fenugreek seeds according to the method of claim 1; and introducing the extract composition into a delivery form.

15. The method as defined in claim 14, wherein the delivery form is selected from the group consisting of a tablet, capsule, powder, granule, microgranule, pellet, soft-gel, controlled-release form, liquid, solution, elixir, syrup, suspension, emulsion, magma, gel, cream, ointment, lotion, transdermal, sublingual, ophthalmic form, nasal form, otic form, aerosol, inhalation form, spray, parenteral form, and suppository.

16. The method as defined in claim 11 wherein the first solvent is selected from the group consisting of hexane, cyclohexane, and ether.

* * * * *